United States Patent [19]
Hayashi et al.

[11] Patent Number: 5,378,429
[45] Date of Patent: Jan. 3, 1995

[54] CORROSIVE ENVIRONMENT SENSOR, CORROSIVE ENVIRONMENT MEASURING APPARATUS AND CORROSIVE ENVIRONMENT CONTROL SYSTEM

[75] Inventors: Makoto Hayashi; Satoshi Kanno, both of Hitachi; Naoto Saito, Niihari, all of Japan

[73] Assignee: Hitachi, Ltd., Tokyo, Japan

[21] Appl. No.: 74,320

[22] Filed: Jun. 9, 1993

[30] Foreign Application Priority Data

Jun. 10, 1992 [JP] Japan .................................. 4-150892

[51] Int. Cl.⁶ ...................... G01N 17/00; G01N 19/08
[52] U.S. Cl. ......................................... 422/53; 73/799; 73/859; 364/508
[58] Field of Search ................. 73/799, 786, 810, 774, 73/859; 364/508; 422/53

[56] References Cited

U.S. PATENT DOCUMENTS

| | | | |
|---|---|---|---|
| 4,003,246 | 1/1977 | Cain | 73/90 |
| 4,149,406 | 4/1979 | Russenberger | 73/775 |
| 4,677,855 | 7/1987 | Coffin, Jr. et al. | 73/799 |
| 4,711,131 | 12/1987 | Hopkins | 73/799 |
| 4,763,528 | 8/1988 | Bouami et al. | 73/799 |
| 4,924,708 | 5/1990 | Soloman et al. | 73/799 |

FOREIGN PATENT DOCUMENTS 3269236 11/1991 Japan .

*Primary Examiner*—James C. Housel
*Assistant Examiner*—Rachel H. Freed
*Attorney, Agent, or Firm*—Antonelli, Terry, Stout & Kraus

[57] ABSTRACT

A corrosive environment sensor comprises an elongate member having a pair of elongate beam portions and a crack growth portion formed between the pair of beam portions so as to extend axially, and a wedge inserted between the pair of beam portions, wherein the crack growth portion has width thereof defined by quadratic curves extending axially so as to decrease from an axially intermediate portion of the sensor member to an axially intermediate portion of the crack growth portion and increase from the axially intermediate portion of the crack growth portion toward an end of the sensor member. The quadratic curves each consist of a first circular arc with first radius between the axially intermediate portion of the sensor member and the axially intermediate portion of the crack growth portion and a second circular arc with second radius less than the first radius between the axially intermediate portion of the crack growth portion and around the second end of the sensor member. There are further disclosed a corrosive environment measuring apparatus employing the above-mentioned corrosive environment sensor, and a corrosive environment control system employing the above-mentioned corrosive environment measuring apparatus.

34 Claims, 19 Drawing Sheets

CORROSIVE ENVIRONMENT SENSOR, CORROSIVE ENVIRONMENT MEASURING APPARATUS AND CORROSIVE ENVIRONMENT CONTROL SYSTEM

BACKGROUND OF THE INVENTION

The present invention relates to a corrosive environment sensor for measuring growth rate of a crack such as corrosion cracking occurring in a corrosive environment, a corrosive environment measuring apparatus for judging corrosive environmental conditions using the corrosive environment sensor and corrosive environment control system using the corrosive environment measuring apparatus, more particularly, it relates to a corrosive environment sensor of double cantilever type and a corrosive environment measuring apparatus, which are suitable to measure growth conditions of a crack in the corrosive environment sensor by a direct current potential method, calculate automatically a crack growth rate from change in the crack length to time and judge corrosion degree in the environment in which the corrosive environment sensor is placed.

In order to measure a crack growth rate in a corrosive environment, it is tentatively tried in a nuclear power plant to measure, by a direct current potential method, the length of a crack caused in a double cantilever type sensor having a load caused therein by applying a fixed displacement thereto. Such a double cantilever type sensor (hereinafter referred to as DCB sensor) has a pair of elongate beam portions opposed to each other and a crack growth portion formed between the beam portions to extend from an axially intermediate portion of each beam portion to a rear end thereof. The crack growth portion extends straightly with a proper width, and the width of the crack growth portion expands around the rear end to be the same as the width of the beam portion. A pre-cracking of a small length is formed at a crack starting end of the crack growth portion by electric discharge machining. The beam portions each have a wedge inserting portion formed around a front end opposite to the rear end to insert a wedge.

In the nuclear power plant, the DCB sensor is disposed in a place of a pressure vessel of a BWR where recirculation water flows. The wedge is inserted in the wedge inserting portion of the DCB sensor thereby to cause displacement in the beam portions and a load in the crack growth portion. Change of a crack occurred in the crack growth portion of the DBC sensor is measured and judged.

This kind of a conventional DCB sensor is disclosed in JP A 62-177440, JP A 2-259555, etc.

Although it is set forth that distribution of stress intensity factor in the conventional DCB sensor is uniform and although the sensor is so long as to be 7 inches in overall length, the DCB sensor has such characteristics that the crack Growth of 1 inch reduces the stress intensity factor to 60% of the initial stress intensity factor, thereby giving rise to a disadvantage that the conventional DCB sensor is not suitable for measuring the crack Growth rate with a proper stress intensity factor.

The inventors proposed previously a DCB sensor which is nearly uniform in the stress intensity factor distribution. A patent application concerning it was filed as U.S. Ser. No. 671,038.

SUMMARY OF THE INVENTION

An object of the present invention is to provide a corrosive environment sensor which is able to keep a stress intensity factor nearly constant even if a crack grows and is capable of precise measurement of a crack growth rate.

Another object of the present invention is to provide an corrosive environment measuring apparatus which is capable of precise automatic calculation of corrosive environment conditions.

To achieve this end, there is provided according to the present invention, a corrosive environment sensor comprising: an elongate member of one piece having a pair of elongate beam portions formed so as to oppose each other and extend axially between both, first and second, ends of the sensor member and a crack growth portion formed between the pair of beam portions so as to extend in a length direction of the sensor member from an axially intermediate portion of the sensor member toward the second end of the sensor member; and a wedge inserted between the pair of beam portions around the first end, wherein the crack growth portion has width thereof defined by quadratic curves extending from the axially intermediate portion of the sensor member toward the second end so as to decrease from the axially intermediate portion of the sensor member to an axially intermediate portion of the crack growth portion and increase from the axially intermediate portion of the crack growth portion toward the second end of the sensor member.

In an aspect of the invention, the quadratic curves each consist of a first circular arc with first radius between the axially intermediate portion of the sensor member and the axially intermediate portion of the crack growth portion and a second circular arc with second radius less than the first radius between the axially intermediate portion of the crack growth portion and around the second end of the sensor member.

Further, there is provided according to the invention a double cantilever type sensor comprising: an elongate metal member having a pair of beam portions formed therein each extending in a length direction from both, first and second, ends of the member and a crack growth portion formed therein and extending in the length direction of the member from a crack terminating end toward the second end, the crack starting end being at an axially intermediate portion between the first and second ends of the member; an expansible wedge disposed between the beam portions around the first end of the member for applying a load to the crack growth portion, the wedge having an expansible chamber; and means for supplying pressurized fluid to the expansible chamber to displace the beam portions so that stress intensity factor at a crack growing point is always constant.

Further, there are provided according to the invention a corrosive environment measuring apparatus employing the above-mentioned corrosive environment sensor, and a corrosive environment control system employing the above-mentioned corrosive environment measuring apparatus.

BRIEF DESCRIPTION OF THE DRAWINGS

FIG. 1b is a front view of the DCB sensor in FIG. 1a;

FIG. 2 is a sectional view taken along a line 2—2 of FIG. 1a;

DESCRIPTION OF THE PREFERRED EMBODIMENTS

Figure 1A:
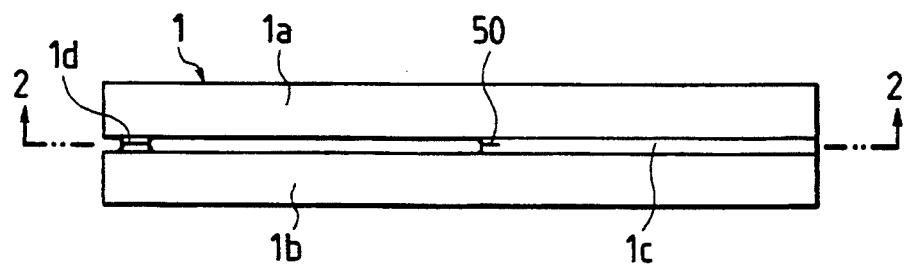
FIG. 1a is a side view of a DCB sensor according to a first embodiment of the present invention.
Figure 1B:
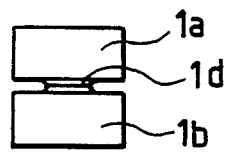

A corrosive environment sensor according to a first embodiment of the present invention will be described hereunder referring to FIGS. 1 to 8.

The corrosive environment sensor is of a so-called type of double cantilever, and, hereunder, it is referred to as DCB sensor. The DCB sensor 1 comprises an elongate member of one piece with a rectangular cross section and a wedge. The member has a pair of beam portions 1a, 1b opposed each other, and a crack growth portion 1c formed between the beam portions 1a, 1b to extend in the length direction from an intermediate between front and rear ends C, B of the beam portion 1a, 1b to the rear end B. At a crack starting end A of the crack growth portion 1c, which is the intermediate of the beam portion 1a, 1b, a pre-cracking 50 is formed by electric discharge machining. The pair of beam portions 1a, 1b each have a wedge inserting portion 1d formed at the front end C (opposite to the rear end B) so as to project oppositely. A wedge 80 (FIG. 9) is inserted in the wedge inserting portions 1d of the beam portions 1a, 1b to cause a fixed displacement in both the beam portions 1a, 1b thereby to impart a load to the crack growth portion 1c.

Figure 4:
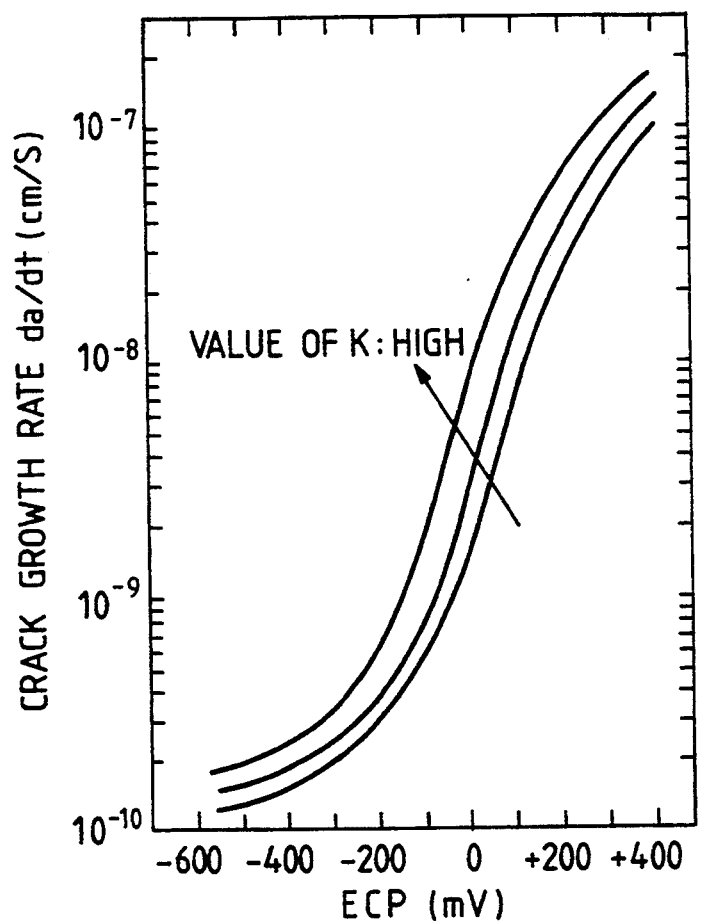
FIG. 4 is a diagram showing the relationship between crack growth rate and electro-chemical potential (ECP)

The DCB sensor 1 is set in a corrosive environment, and a growth rate of a crack caused in the crack growth portion 1c is measured by a direct current potential method. The crack growth rate is larger when corrosive conditions of the environment are worse, and smaller when the corrosive conditions are better. The crack growth rate depends on a stress intensity factor and the corrosive degree of the corrosive environment. In case of the same stress intensity factor, the crack growth rate is fast when the concentration of dissolved oxygens, for example, in the corrosive environment is high, on the contrary, it is slow when the concentration of dissolved oxygens is low. As shown in FIG. 4, the crack growth rate is fast when water environment is bad and corrosive potential (ECP) is high while the rate is slow when the EPC is low. On the other hand, the higher the stress intensity factor, the faster the crack growth rate. Accordingly, by disposing the DCB sensor 1 having a proper stress intensity factor set by the wedge 80 in a corrosive environment, measuring the length of a crack, and obtaining the crack growth rate, a corrosive degree of the corrosive environment Can be found from the crack growth rate.

In conventional sensors of this kind, however, stress intensity factor decreases as crack grows. Therefore, it is necessary to evaluate a corrosive degree of the corrosive environment, taking account of both the stress intensity factor and the crack growth rate.

Figure 9:
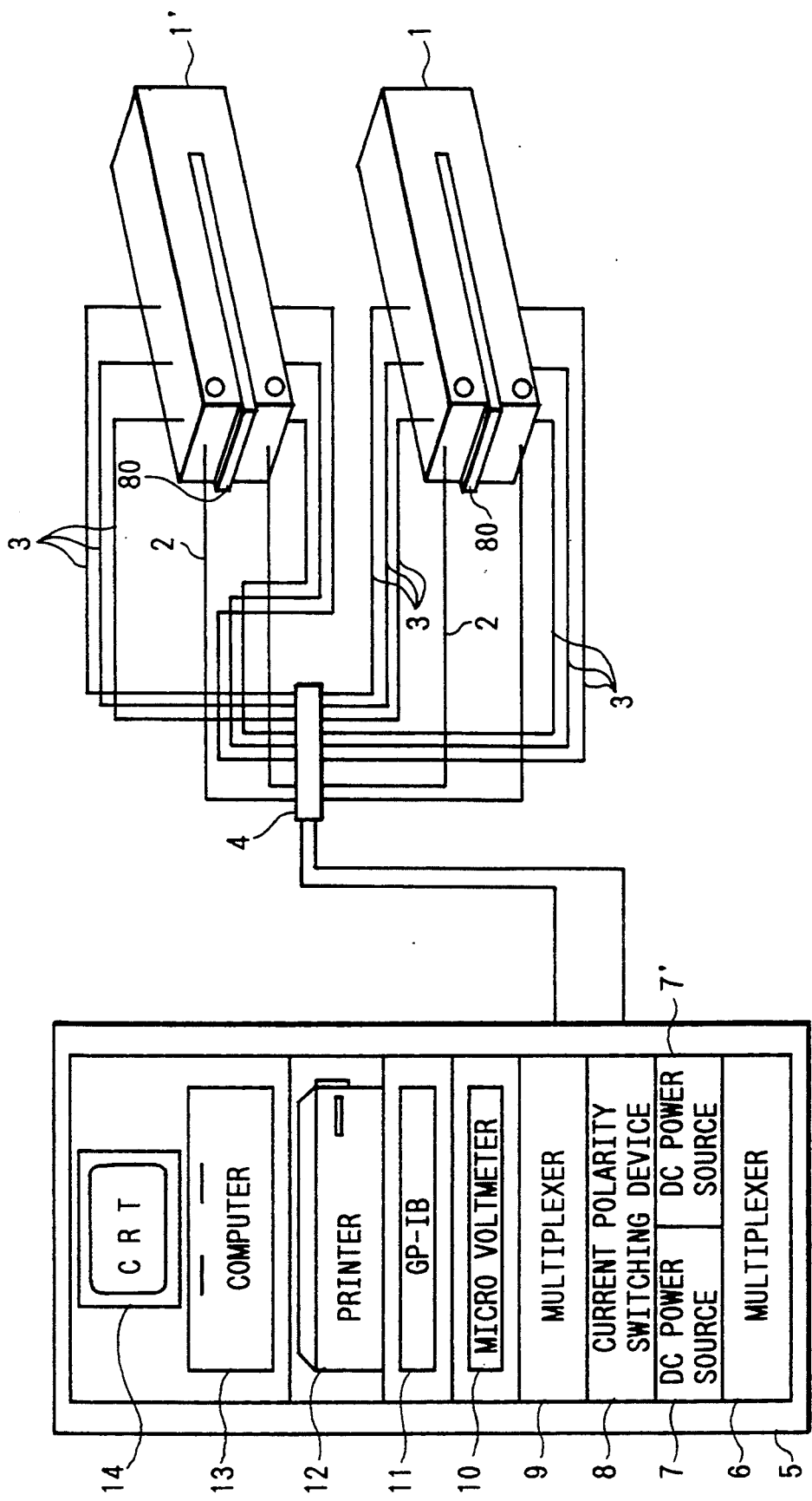
FIG. 9 is a schematic diagram for explanation of a corrosive environment measuring apparatus employing the corrosive environment sensor.

On the contrary, in the DCB sensor the length of which is sufficiently long from the wedge portion to the crack starting end of the crack growth portion, as shown in FIG. 9, the stress intensity factor at the crack growing tip portion of the crack growth portion does not change so much even if a crack grows, but when the length is not sufficiently long, the stress intensity factor decreases drastically as the crack grows. Without a sufficient stress intensity factor, the crack will not grow. In this case, since the stress intensity factor decreases the growth stops when the crack grows to a certain extent, and the sensor will cease to function as a corrosive environment sensor. When the wedge is thickened to make the stress intensity factor larger so that the extended crack grows further, the crack grows rapidly and the life of the sensor is shortened. Further, unless the DCB sensor is small in size, the sensor can not be inserted in a LPRM equipped in a BWR.

In the DCB sensor 1 according to this embodiment, the sides of the crack growth portion defining its width each are formed in quadratic curve and the width of the crack growth portion 1c decreases gradually along quadratic sides with a first radius from a crack starting end thereof to the intermediate portion between the axial ends A, B of the crack growth portion 1c and increases along the quadratic sides with a second radius smaller than the first radius from the intermediate portion to the crack termination end B.

Figure 2:
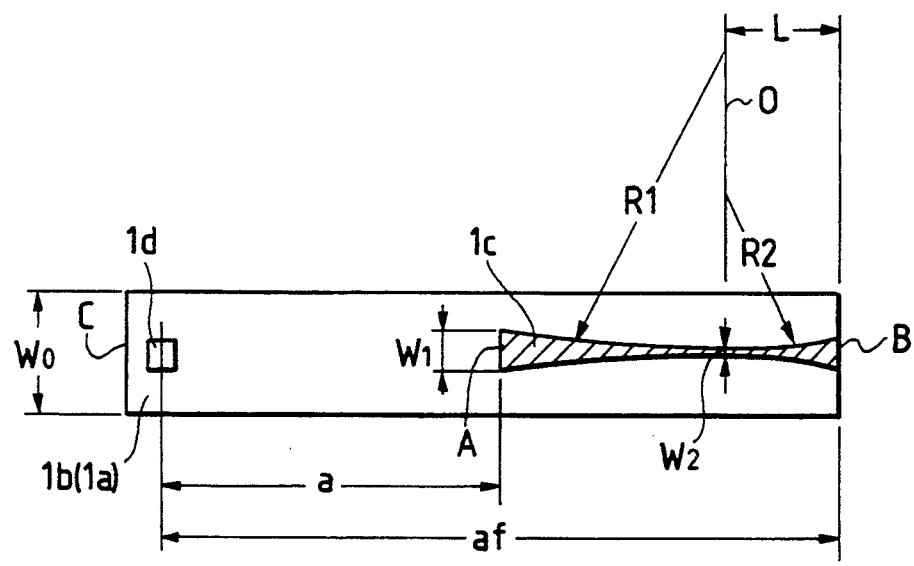

As in FIG. 2, the width of the crack grow portion is defined by the sides each of which has a first arc-shape with a first radius R1 the center of which is on a center line O spaced by distance L from the crack termination end B toward the crack starting end A, and a second arc-shape with a second radius R2 the center of which is on the above-mentioned center line O. The width gradually decrease along the first arc-shaped sides from the crack starting end A to the center line O and increases from the center line O to the crack termination end B.

An example of numerical values is described hereunder. When the corrosive environment sensor 1 has a width Wo of 15 mm, a length L, from the wedge insertion portion 1d to the crack starting end A, of 15–20 mm, a minimum width W2 of the crack growth portion 1c is made to be 2 mm. The width is made into a tapered shape formed by combining a first arc-shaped side of the first radius R1 of 100–160 mm and a second arc-shaped side of the second radius 60–75 mm, as shown in FIG. 2.

The DCB sensor 1 is necessary to have a stress corrosion cracking caused sufficiently in a corrosive environment. Therefore, it is desirable to select a material which is high in yield stress and sensibility of stress corrosion cracking through a stress corrosion cracking test conducted in advance in an experiment room and produce the sensor with the same material as the selected material. As a material for the DCB sensor 1, stainless steel of SUS 304 having carbon content of 0.05% or more is desirable. In this case, when the material is taken from raw material, a taking method may influence stress corrosion cracking growth.

Figure 3:
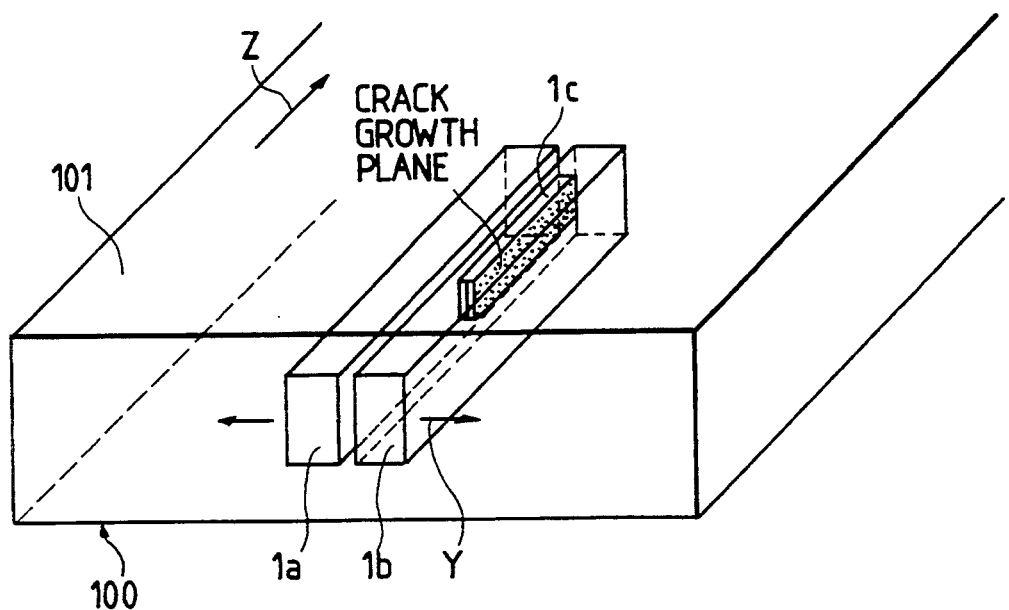
FIG. 3 is an explanation view for producing a DCB sensor from a rolled plate.

Therefore, as shown in FIG. 3, a stainless steel with C of 0.05% or more is rolled to form a rolled plate 100. A member for the DCB sensor 1 is taken from the rolled plate 100 in such a manner that the rolling direction Z of the rolled plate 100 is the same as the direction of crack growth of the crack growth portion 1c, a displacement imparting direction Y is perpendicular to the rolling direction Z. Namely, in order to produce the corrosive environment sensor 1 from the rolled stainless steel plate 100, the beam portions 1a, 1b are formed so that the length direction of the beam portion is in the rolling direction Z of the rolled plate 100, and the displacement imparting direction Y is in parallel to the rolled surfaces 101 of the rolled plate 100 and perpendicular to the rolled direction Z.

Figure 5:
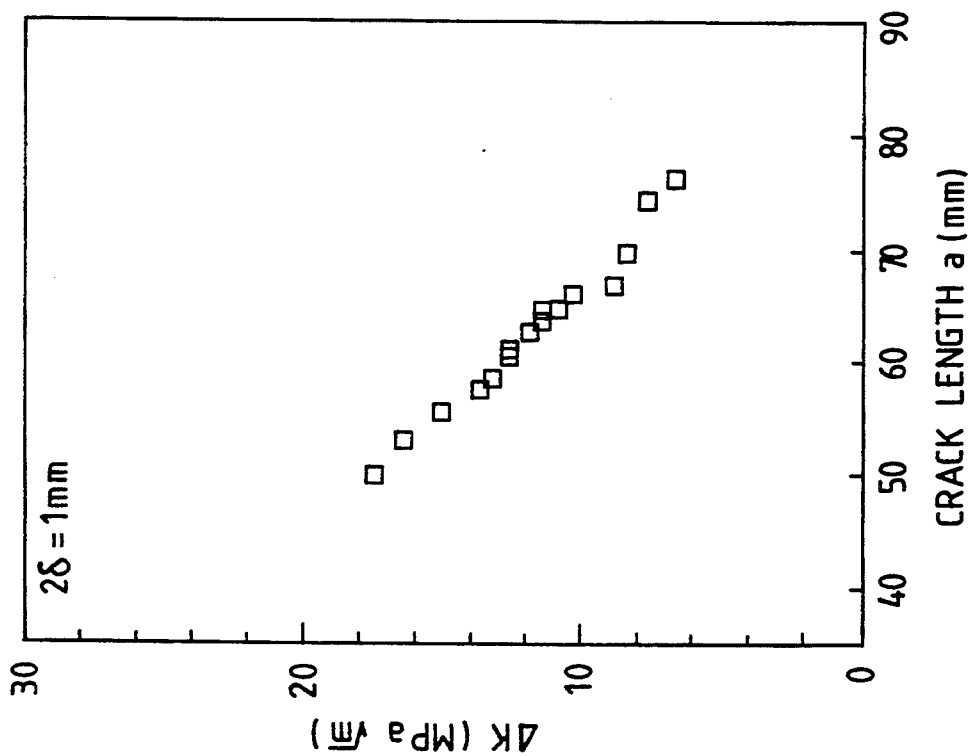
FIG. 5 is a diagram for explanation of the relationship between stress intensity factor and crack length in a conventional corrosive environment sensor.

Before describing an operation of the DCB sensor 1 according to this embodiment, a conventional DCB sensor having a fixed width of a crack growth portion will be described hereunder referring to FIG. 5. FIG. 5 shows change of stress intensity factor $\Delta K$ in accordance with crack length a, which is obtained through a fatigue test with a fixed amplitude. In FIG. 5, the stress intensity factor $\Delta K$ is nearly 18 MPa$\sqrt{m}$ when the crack length a is 50 mm, however, the stress intensity factor decreases rapidly as the crack length a becomes long, it is decreases to about 6 MPa$\sqrt{m}$ when the crack length a is 75 mm, and it decreases to less than 4% of the stress intensity factor at an initial cracking.

Figure 6:
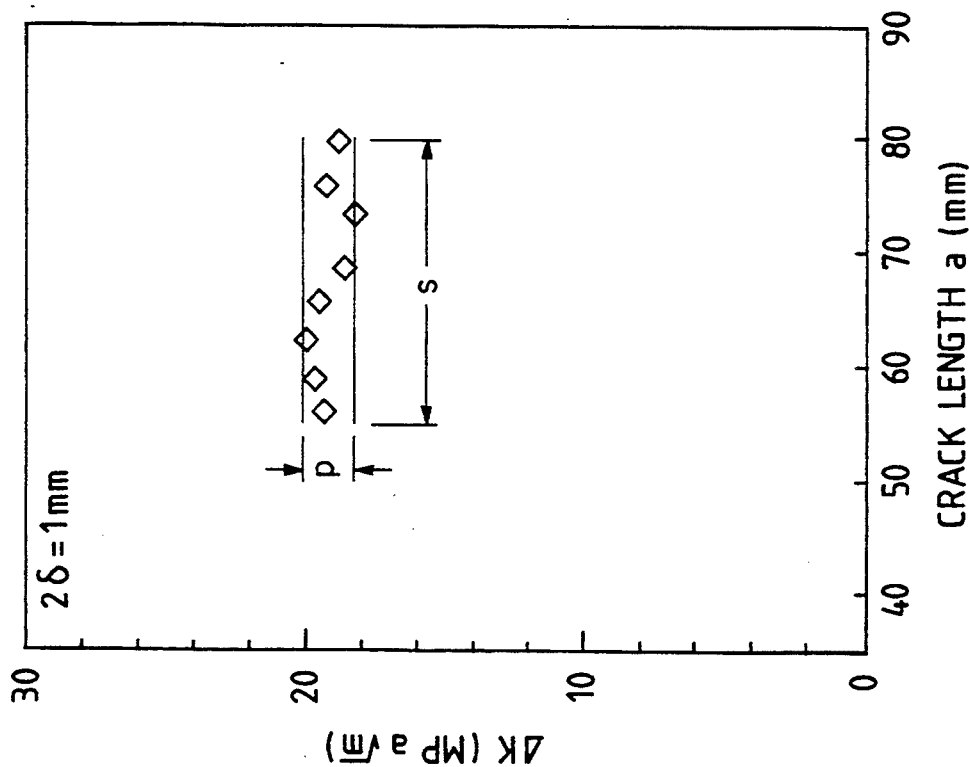
FIG. 6 is a diagram for explanation of the relationship between stress intensity factor and crack length in the corrosive environment sensor of the first embodiment of the present invention.
Figure 7:
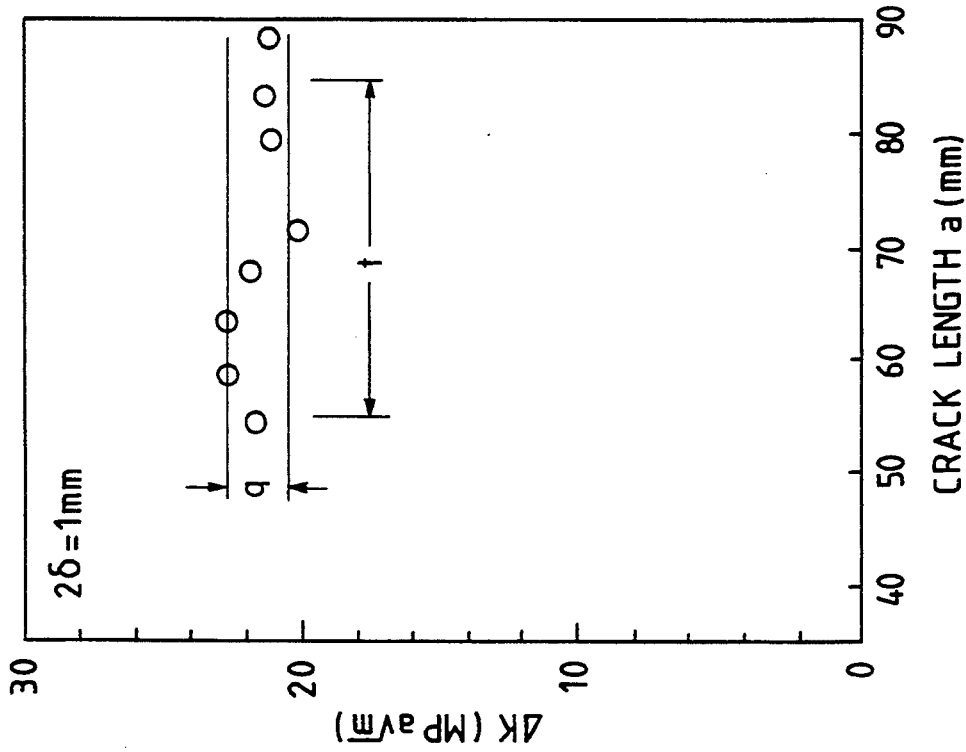
FIG. 7 is a diagram for explanation of the relationship between stress intensity factor and crack length when the crack growth portion of the corrosive environment sensor changes variously in minimum width and radius.

Next, the DCB sensor 1 according to the embodiment is described referring to FIGS. 6 and 7.

FIGS. 6 and 7 show change of stress intensity factor in accordance with change in crack length, which is obtained through a fatigue test with a fixed amplitude being applied. In the DCB sensor 1, when crack length a of the crack growth portion 1c extends from the crack starting end A to the minimum width portion W2 which is on the way to the crack termination end B, the stress intensity factor $\Delta K$ increases gradually since the DCB sensor 1 has the width and cross sectional area, of the crack growth portion, both decreasing gradually from the crack starting end A to the minimum width portion, and the stress intensity factor $\Delta K$ is prevented from expanding too much since the width of the crack growth portion 1c expands from the minimum width portion toward the crack termination end B to increase gradually the crosssectional area. Therefore, as the crack length of the crack growth portion 1c extends, a little change occurs in the stress intensity factor $\Delta K$. However, the stress intensity factor $\Delta K$ can be kept substantially constant. Namely, the stress intensity factor âóK can be kept substantially constant irrespective of growth in a crack.

In FIGS. 6 and 7, the stress intensity factor $\Delta K$ is within a variation range of 10% or less when the crack length change $\Delta a$ is within a range of 25 to 30 mm. In FIG. 6, "p" is 10%, and "s" is 25 mm. Therefore, the stress intensity factor $\Delta K$ is substantially constant. The absolute value of the stress intensity factor $\Delta K$ in FIG. 7 is a little larger than that in FIG. 6. This is for the reason that the minimum width W2 in FIG. 7 is a little smaller and the radius R1, R2 are little larger. In FIG. 7, "q" is 10% and "t" is 30 mm. Further, data in FIGS. 6, 7, are obtained from the DCB sensor 1 which is constructed, based on dimensional data selected from a width W0 of 15 mm, a distance L of 15–20 mm to a length af of 100 mm, a minimum width W2 of 2 mm, a first radius R1 of 110–160 mm, and the second radius R2 of 60–75 mm.

Figure 8:
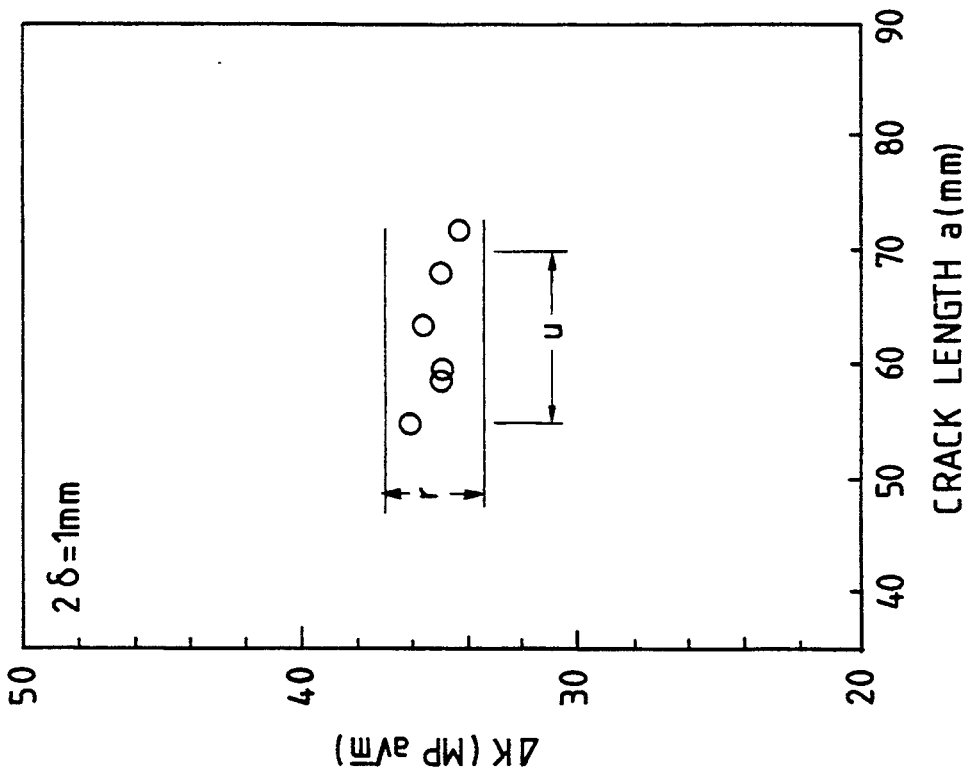
FIG. 8 is a diagram for explanation of the relationship between stress intensity factor and crack length in the corrosive environment sensor in which the crack growth portion takes further reduced width.

Further, in the DCB sensor 1, bending moment applied on the beam portions 1a, 1b can be reduced by thinning the thickness of the wedge 80. Namely, referring to FIG. 8 showing the relationship between the stress intensity factor $\Delta K$ and crack length a when the corrosive environment sensor 1 has the minimum width W2 of 1 mm, the first radius R1 of about 180–220 mm, the second radius R2 of 90–100 mm and the other parts the dimensions of which are the same as the previously mentioned, it is found that the stress intensity factor $\Delta K$ is within a variation range of 10% or less when the crack length change $\Delta a$ is within a range of 15 mm. In FIG. 8, "r" is 10% and "u" is 15 mm. In this case, the absolute value of the stress intensity factor ΔK when the same amplitude is applied is larger by about 75%, compared with FIGS. 6, 7, which corresponds to a reduced width amount in the minimum width W2, so that the bending moment applied on the beam portions 1a, 1b can be reduced surely by thinning the wedge width by an amount corresponding to the reduced width amount.

The minimum width W2 can not be reduced extremely. This is for the reason that even if the first and second radius R1, R2 of the crack growth portion 1c are reduced to keep plane strain conditions, it is forecast that it is difficult to keep the plane strain conditions for a long time and that structure sensibility of the sensor material appears in a crack growth rate of corrosion stress cracking when the minimum width is extremely small. Accordingly, it is preferable that the minimum width W2 is 1 mm or larger even if the width is reduced.

Further, when the DCB sensor 1 is used in a BWR, the sensor 1 is exposed to pure water of about 300° C. in fact. Even at such a high temperature, when bending moment applied on the beam portions 1a, 1b is large, relaxation takes place by creep, and the stress intensity factor at the cracking tip portion decreases. In order to suppress the defect it is desirable that the width of the cross section in which the crack grows is 20% or less of the width of the sensor. Namely, maximum width W1 of the crack growth portion 1c is equal to or less than 0.2 times the sensor maximum width W0. In similar meaning, it is more effective for reduction prevention of the bending moment applied on the beam portions 1a, 1b to make the height of the sensor 1 larger than the sensor width.

The corrosive environment sensor 1 made from rolled stainless steel plate 100 containing 0.05%C or more is excellent in reaction of stress corrosion cracking and high in yield stress, so that the sensor can be used in the pure water of high temperature of about 300° C.

A corrosive environment measuring apparatus employing DCB sensors 1, 1' is described referring to FIGS. 9 to 15.

In FIG. 9, two current supply leads 2 for supplying current to prescribed positions of the surface of the DCB sensors 1, 1' and measuring leads 3 for measuring potential difference are connected to the sensors, respectively, by spot welding. One ends of the current supply leads 2 are welded to the tip surface of the sensor 1, 1' and the other ends to a multiplexer 6 of a corrosive environment measuring apparatus 5 through a terminal box 4, and electric current from two direct current electric sources 7, 7' are switched intermittently by a polarity reverse or switching device 8 and supplied to the sensors 1, 1'. The measuring leads 3 have one ends connected to upper and lower surfaces of the sensors 1, 1' with prescribed distances therebetween at the front ends of the sensors 1, 1', the other ends connected to multiplexer 9 for measuring potential differences. Measuring positions are reversed by the multiplexer 9 and potential difference is measured by a micro voltmeter 10. The measured potential difference is transmitted to a computer 13 through a GP-IB interface 11. When the measurement commences, the computer 13 calculates and records, in a manner set forth later, crack length of the censors 1, 1' from test or operation time data and the potential differences, measured at fixed time intervals. Crack growth curves are obtained from the results, crack growth rates are calculated from gradients of the crack growth curves, and the relationship between the crack growth and stress intensity factor is obtained. The result is displayed on a frame of a CRT 14 and/or outputted by a printer 12. The computer 13 controls the current polarity reverse device 8 and the multiplexer 6, 9 through the GP-IB interface 11.

The corrosive environment measuring apparatus 5 is further explained hereunder.

Figure 10:
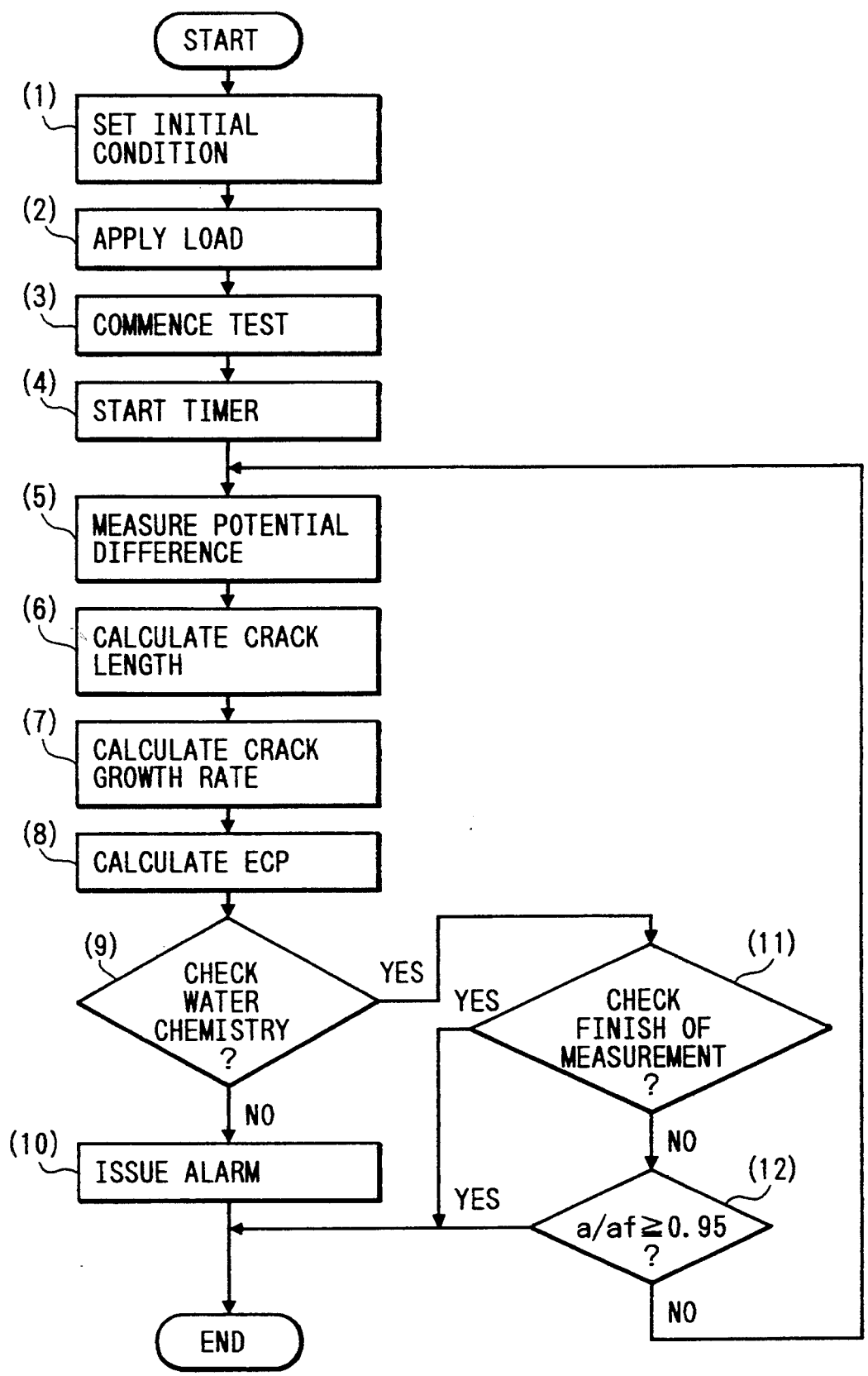
FIG. 10 is a flow chart of a control operation of the corrosive environment measuring apparatus.

Referring to FIG. 10, in step 1, initial conditions are set including mounting of DCB sensors 1, 1' and setting of temperature and water chemistry of a corrosive environment. In step 2, the wedges 80 each are inserted in the DCB sensors 1, 1' to apply a fixed displacement to the sensors thereby causing a load in each crack growth portion 1c. Then, a test is commenced in step 3. In step 4, a counter for counting test time, for example, timer for measuring 16 hours is started at the commencement of the test. In step 5, potential differences of the DCB sensors 1, 1' are measured, crack length ratio a/af is calculated.

Then, in step 7, a crack growth rate is calculated, and electro-chemical potential (ECP) is calculated using the relationship characteristic curve as shown in FIG. 4 in step 8. In this case, the ECP is attained from the characteristic curves of the relationship between the crack growth rate and ECP shown in FIG. 4 on the basis of the crack growth rate calculated in the step 7 and the stress intensity factor imparted on the DCB sensors 1, 1' by the wedges 80. And then, in step 9, check of a corrosive environment, in particular, check of dissolved oxygen concentration is effected on the basis of the results of the attained ECP.

As a result, when the water chemistry is abnormal, an alarm is issued in step 10 to interrupt the measurement or output a signal for injecting hydrogens into the water to turn the water chemistry into a normal condition, for instance. On the other hand, when the water chemical is normal, whether or not the measurement is terminated is checked in step 11. When the measurement is kept on, the crack length a to the length af of the DCB sensor 1, that is, a/af is checked on whether or not it exceeds an allowed value of 0.95 which is predetermined, in step 12, and the operations from step 5 to step 12 are repeated. When the crack length a/af becomes the allowed value or more, the operation is ended.

Figure 11:
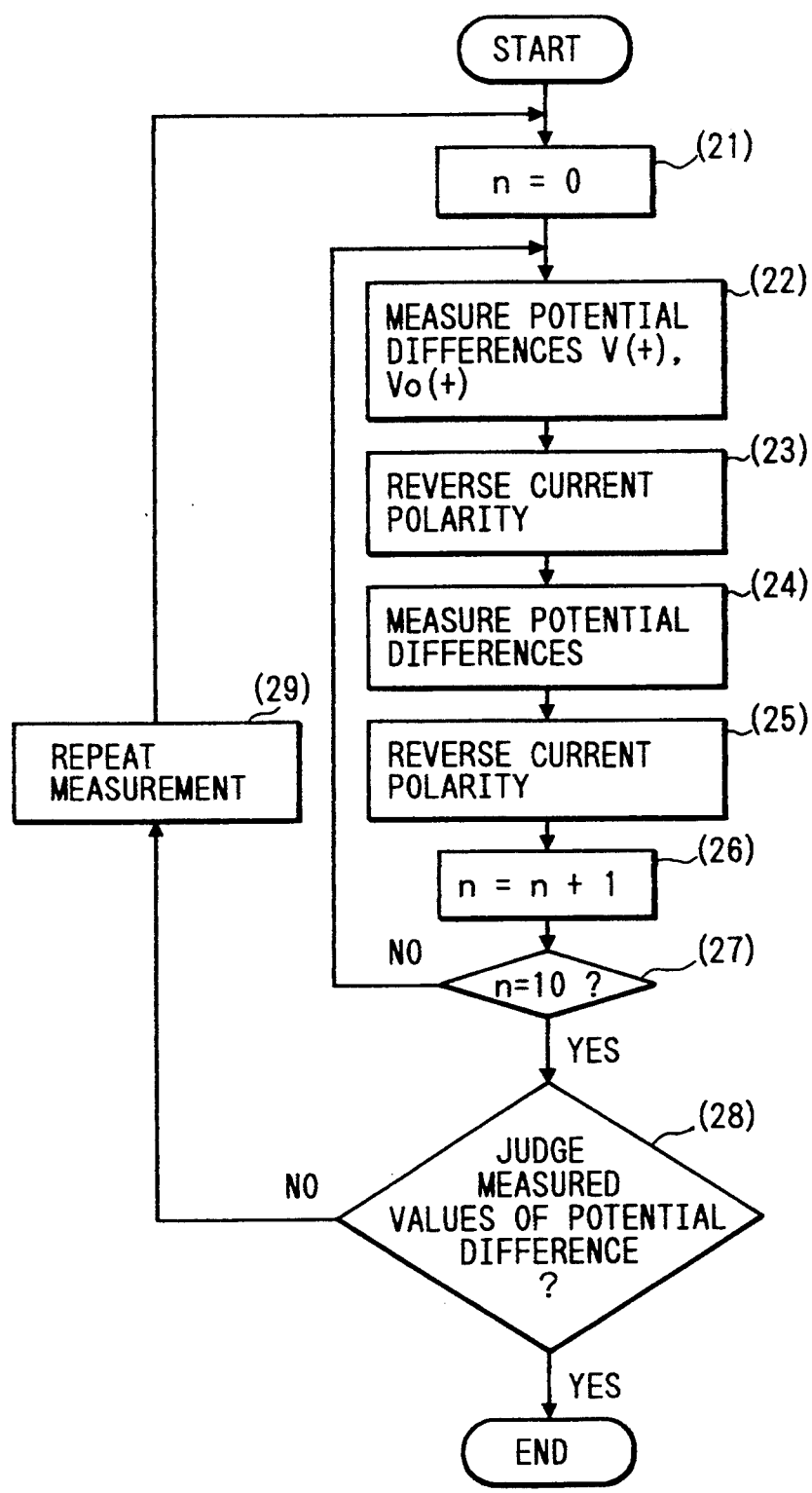
FIG. 11 is a flow chart of potential difference measurement.

The corrosive environment measuring apparatus 5 is further explained in detail referring to a flow chart of FIG. 11.

In FIG. 11, in step 21, the number of measuring times n of potential difference is set as n=0, then, in step 22 potential difference V0 (+) and V (+), induced when electric current + is applied to the DCB sensors 1, 1' from the direct current sources 7, 7', is measured by the micro voltmeter, the polarity of the current to be supplied is reversed by the current polarity reversing device 8 in step 23 to supply current of negative (−) to the DCB sensors 1, 1', and then the potential difference V0(−) and V(−) are measured in step 24.

In step 25, the polarity of the current is reversed to return to the initial polarity. In step 26, the number of measuring times is counted, and then it is judged whether or not the number of measuring times reach a predetermined one, for example, 10 times. As a result, if the number of measuring times do not reach the predetermined one, the operations after the step 22 are repeated. When it reaches the predetermined numbers, it is judged whether or not measured values of the potential difference which are attained until now is normal in step 28. In this case, when the measured value of potential difference is normal, the measurement is ended, but when it is abnormal, the measurement is effected again in step 29 to execute repeatedly the operations after the step 21.

Figure 12:
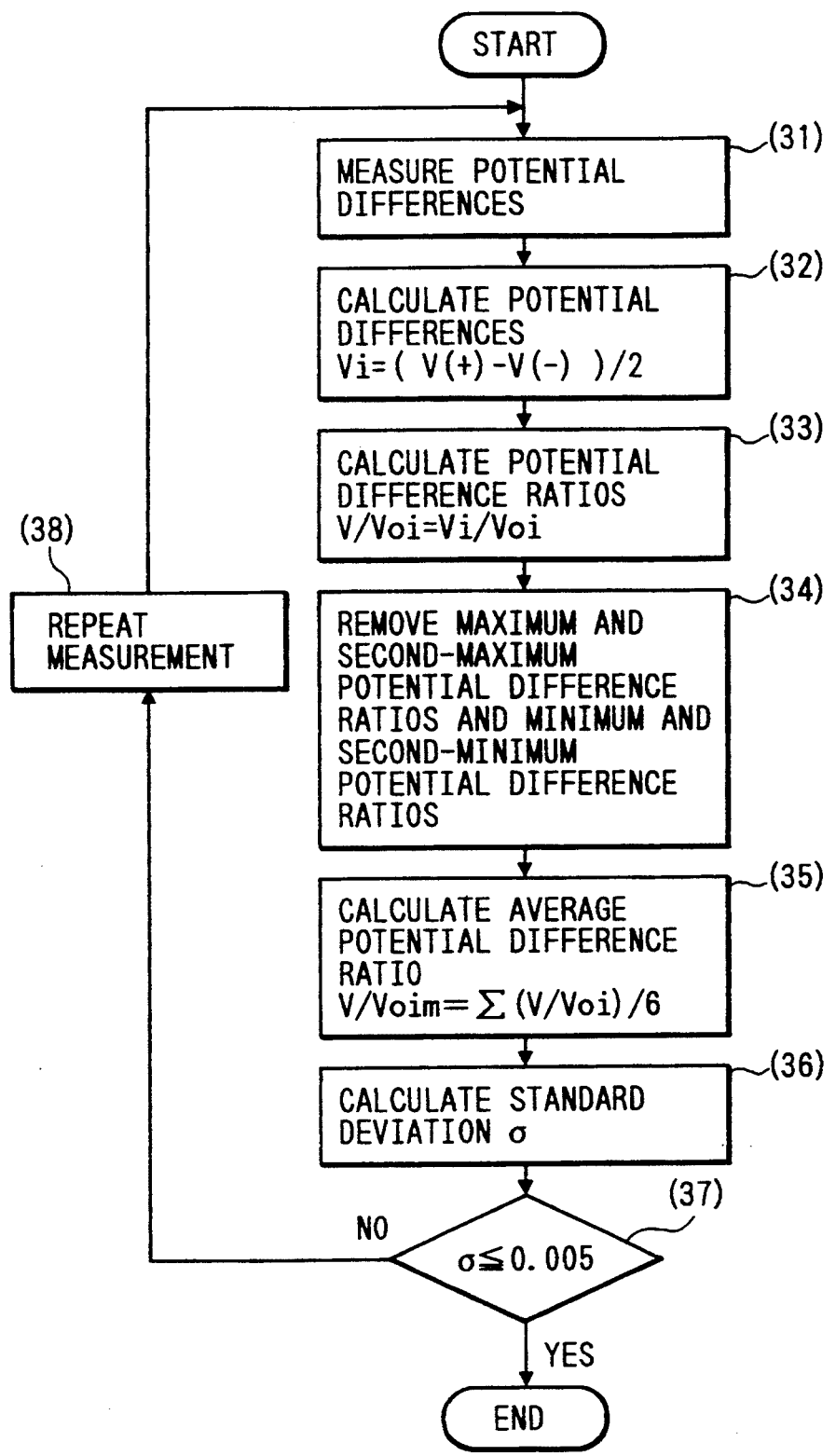
FIG. 12 is a flow chart of subroutine of judgment of values of the potential difference measurement.

FIG. 12 is a flow chart of a subroutine for judging the measured value of potential difference.

In FIG. 12, in step 31 potential difference is measured as in FIG. 11, and then amplitudes of the measured potential difference $Vi=(V(+)-V(-))/2$ and $Voi=(Vo(+)-Vo(-))$ are calculated in step 32. Next, in step 33, potential difference ratio $V/Voi=Vi/Voi$ is calculated from the calculated amplitudes of potential difference.

In step 34, four (4) potential difference ratios, that is, the maximum potential difference ratio, the next maximum potential difference ratio, the minimum potential difference ratio and the next minimum potential difference ratio are removed from ten (10) potential difference ratios obtained in the previous steps, taking account of variation in the potential difference measurement. In step 35, an average potential difference ratio $V/Vom=\Sigma(Vi/Voi)/6$ is calculated from the remaining six (6) potential difference ratios. In step 36, a standard deviation $\sigma$ of the potential difference ratios is calculated, based on the calculated average potential difference ratio. In step 37, it is judged whether or not the standard deviation $\sigma$ is a reference value 0.005 (in this example) or less. As a result of the judgment, if the standard deviation $\sigma$ is larger than the reference value, the measurement is judged to be abnormal, operations after the step 31 are executed through remeasurement in step 38, and the standard deviation $\sigma$ is the reference value or less, the execution is ended.

Figure 13:
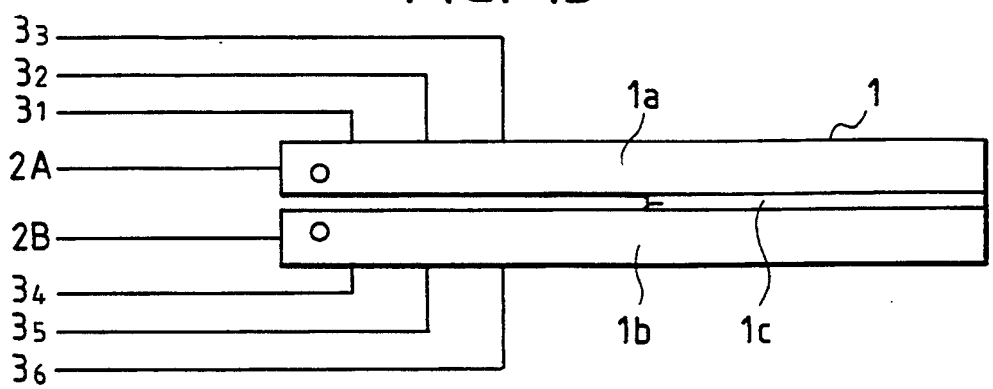
FIG. 13 is a schematic diagram showing connection of current supply leads, measuring leads and beam portions of the corrosive environment sensor.
Figure 14:
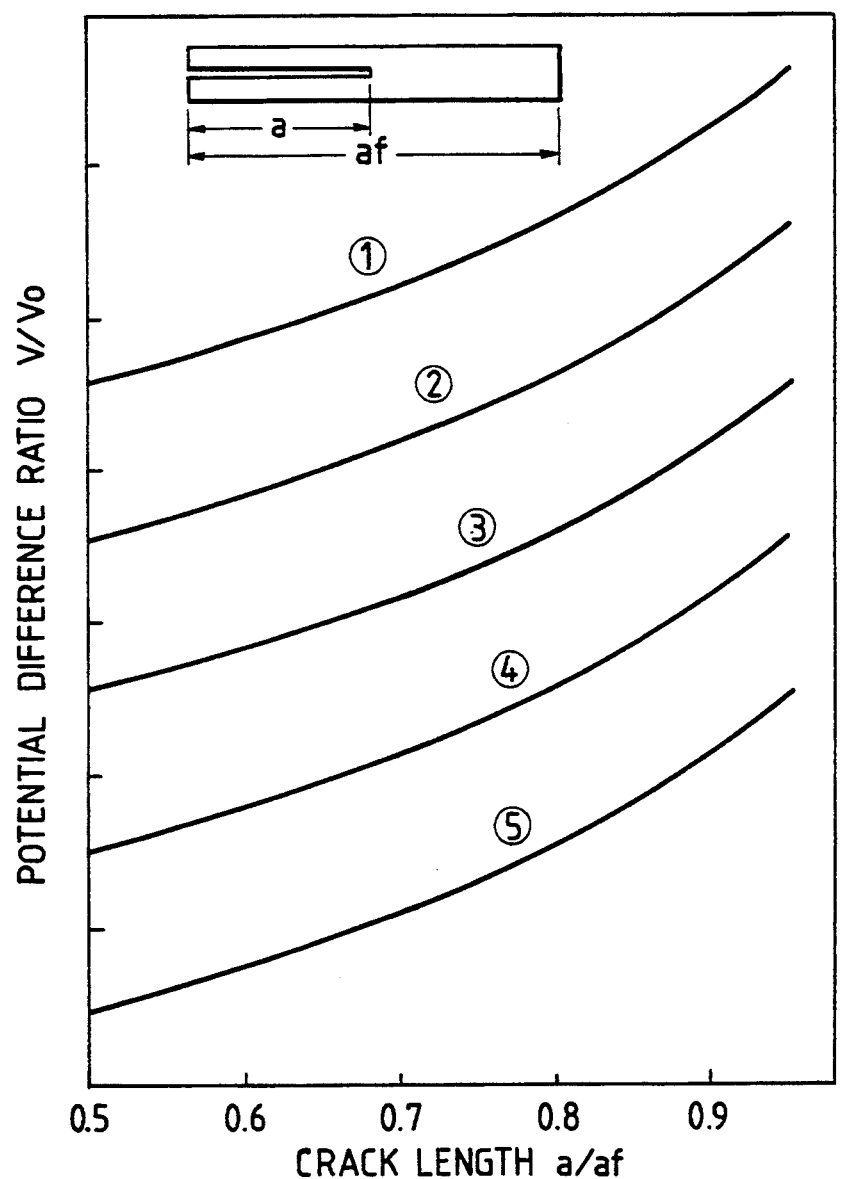
FIG. 14 is a diagram showing master curves of judgment of crack length.

Next, measurement of crack length by potential difference measurement is explained referring to FIGS. 13, 14.

In FIG. 13, current supply leads 2A, 2B for measuring potential difference are welded to central portions of tips of the beam portions 1a, 1b of the DCB sensor 1 by spot welding, respectively. Each three of measuring leads $3_1-3_6$ for measuring potential difference are connected to outside surfaces of the beam portions 1a, 1b so as to oppose each other. Potential difference is detected between the measuring leads. For instance, potential differences V12, V13, V14, V15, V16, V23, V24, V25, V26, V34, V35, V36, V45, V46, V56 are to be measured, wherein symbols V, for example V14, V15 are potential between leads $3_1-3_4$, potential between $3_1-3_5$, respectively. Since distances between the measuring leads $3_1-3_3$ and $3_4-3_6$ are made equal and the measuring leads $3_1-3_3$ and the measuring leads $3_4-3_6$ are arranged symmetrically, basically, the potential difference between the measuring leads have the following relations;

$$V12=V23=V45=V56, V13=V46, V15=V24, V16=V34, V26=V35.$$

However, actually, some difference occurs in potential difference due to errors in mounting distances of the leads. Therefore, in order to raise preciseness in measurement of the crack length, it is most suitable to measure many potential differences, obtain crack length using a master curve between the potential differences and crack length, and calculate crack length from the average.

On the other hand, the potential differences are influenced by temperature, in addition to the material from which the DCB sensor 1 is made. As a method of avoiding the influence of temperature and material, there is considered a method in which when two potential differences Vo, V between positions are measured and ratio V/Vo is used letting one of them be a standard potential difference Vo, a master curve between the potential difference ratio V/Vo and the crack length is not influenced by temperature and material. In case of DCB sensor 1, as a standard potential difference, there are six, that is, $Vo=V12\approx V23\approx V45\approx V56$, $Vo'=V13\approx V46$, and as operational potential differences, there are nine, that is, $V=V14$, $V15\approx V24$, $V16\approx V34$, V25, $V26\approx V35$, V36. Therefore, in total, there are combinations of potential differences $(6\times 9=54)$. As mentioned above, the standard potential difference is $Vo=V12=V23=V45=V56$, or $Vo'=V13=V46$, that is, two. Further, since $Vo'=2Vo$, the standard potential difference is one, basically.

The operational potential differences V are five, that is, V14, V15=V24, V16=V34=V25, V26=V35, V36, so that the total master curves of potential difference ratio V/Vo and crack length are sufficient to be five $(1\times 5)$.

Further, basically, there are the following relations;

$$V14=V36+4Vo$$

$$V15=V24=V36+3Vo$$

$$V16=V25=V34=V36+2Vo$$

$$V26=V35=V36+Vo,$$

so that it is sufficient to make only one master curve of potential difference ratio V36/Vo and crack length a.

FIG. 14 is a graph showing characteristics of master curves used for judging the length obtained through electric field analysis using the finite-element method. The ordinate represents the potential difference ratio V/Vo and the abscissa represents the crack length a/af normalized by the length af of the DCB sensor. Curves 1, 2, 3, 4 and 5 correspond to $V/Vo=V14/V12$, $V/Vo=V15/V12$, $V/Vo=V16/V12$, $V/Vo=V26/V12$ and $V/Vo=V36/V12$, respectively. Each master curve is usually approximated with an fifth power equation and the approximate equation obtained thereby is used for converting the potential difference ratio V/Vo into the crack length a/af. This converting method is described in the earlier U.S. patent application by the same inventors.

Figure 15:
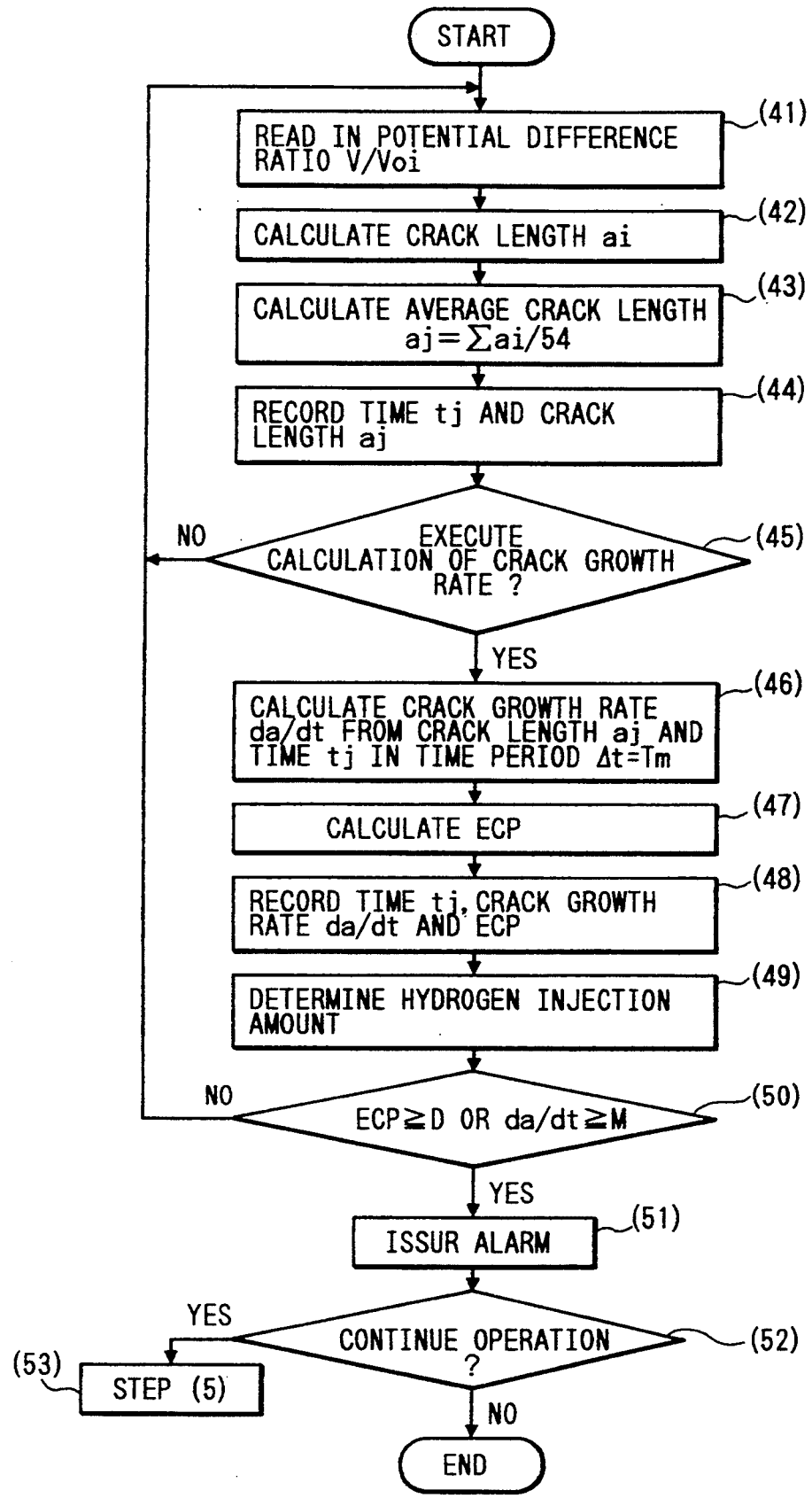
FIG. 15 is a flow chart of subroutine for calculation of crack growth rates and electro-chemical potentials.
Figure 16:
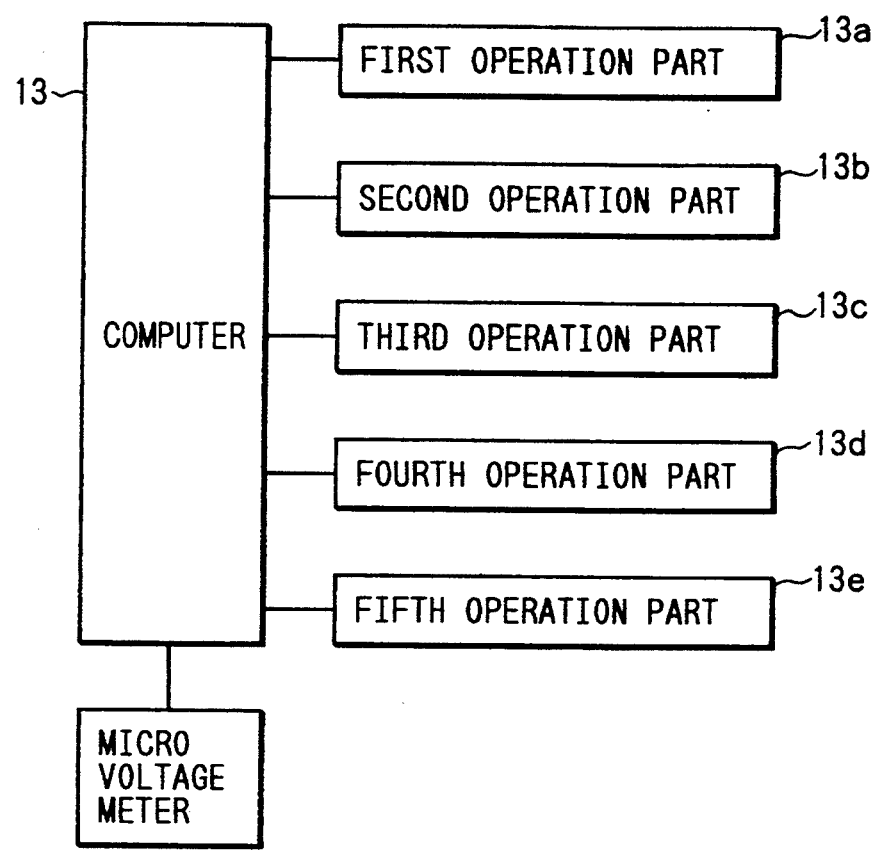
FIG. 16 is a block diagram of computer functions.

After a series of crack length measurement have been finished, it becomes necessary to perform the data processing as shown in FIG. 15 by the computer 13 in FIG. 9. The measurement is controlled by the computer 13 so that it is possible to perform the data processing.

Figure 17:
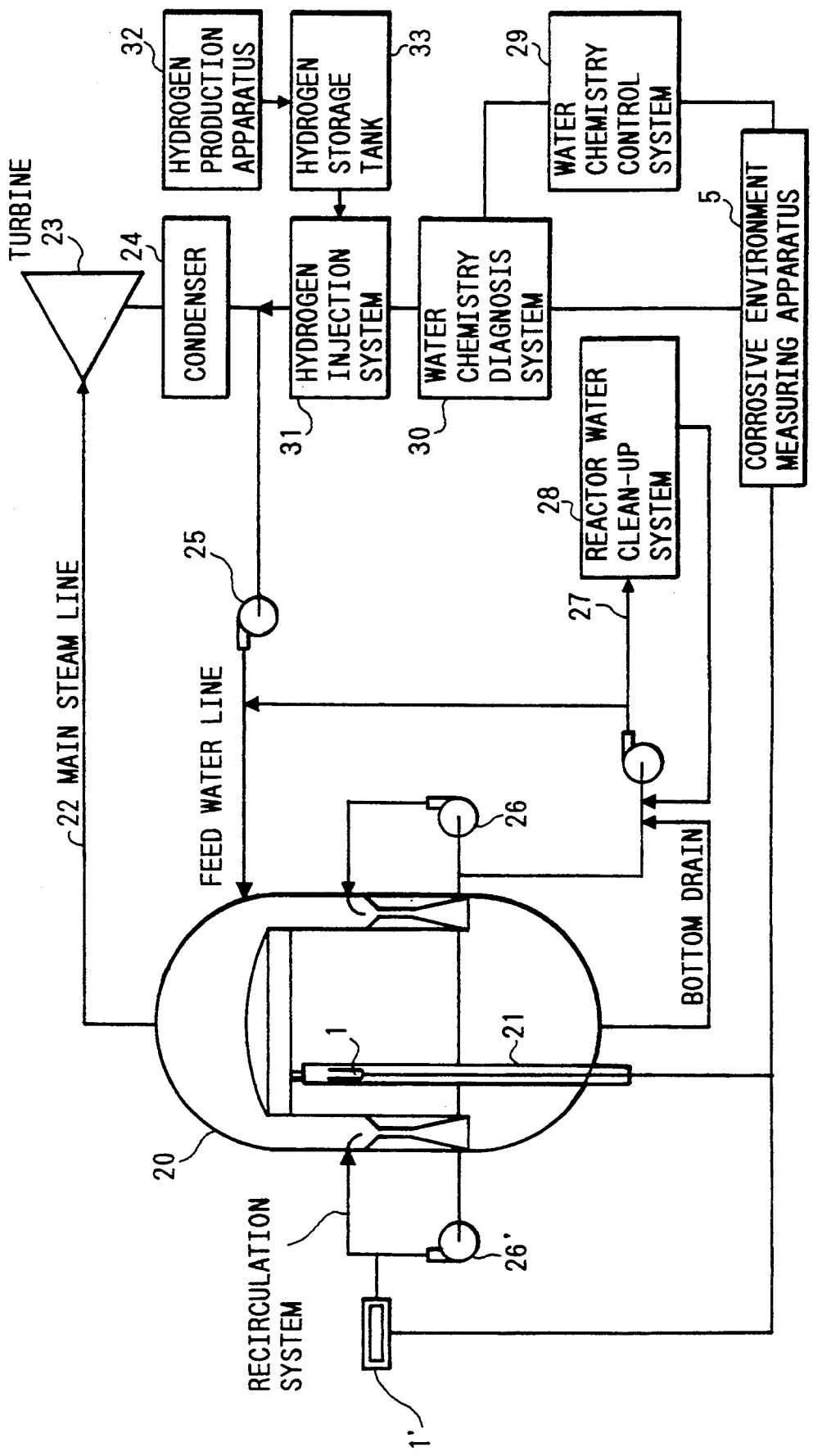
FIG. 17 is a block diagram of a corrosive environment control system employed in a nuclear power plant.

FIG. 15 is a flow chart showing the process of judging the crack length, calculating the crack growth rate and measuring the corrosive environment, it further includes a part of a corrosive environment control as shown in FIG. 17 such as water chemistry control by hydrogen injection into the water.

Referring to FIG. 15, in step 41, the potential difference ratios V/Voi are read. In step 42, crack length ai is calculated on the basis of the master curves of FIG. 14 and the potential difference ratios. In step 43, an average crack length aj is calculated in accordance with the equation$(\Sigma ai/54)$ from the obtained crack length ai. In step 44, the average crack length aj and crack length measuring time tj are recorded. The crack growth rate should not necessarily be calculated each time the crack length is measured but may be calculated at regular certain time intervals. In step 45, it is judged whether or not the crack growth rate is to be calculated, and if it is judged not to be calculated, the operation returns to the step 41. If it is judged that the crack growth rate is to be calculated, the operation proceeds to step 46 in which a crack growth rate da/dt is calculated with a first power equation by a least squares method using the data on the crack length aj and time tj obtained and measured within a fixed time period $\Delta t = Tm$. Then, in step 47, corrosive potential ECP is calculated from the crack growth rate using the relationship shown in FIG. 4. In step 48, the time tj, the crack growth rate da/dt and the ECP are recorded. In step 49, in case the apparatus 5 is used for corrosive environment control, a hydrogen injection amount is determined in accordance with the crack growth rate da/dt and the ECP. Basically, the hydrogens are injected so as to satisfy the following relation; $da/dt \leq 2 \times 1/10^9$ mm/sec or ECP $\leq -250$ mV. In this case, even if the hydrogens are injected, the concentration of dissolved oxygens is not necessarily reduced soon. Further, hydrogen injection too much is not effective so much. Therefore, the upper limit of an amount of hydrogen to be injected is 2 ppm.

After injection of hydrogens, in step 50 the corrosive environment is Judged according to the judgment reference, ECP$\geq$D or da/dt$\geq$M, wherein symbols D and M represent critical values in ascertaining whether the environment is good or not. As a result of judgment in step 50, if ECP<D and da/dt<M, the operations after step 41 are repeated. On the other hand, if ECP$\geq$D or da/dt$\geq$M, an alarm is issued in step 51. In step 52, it is Judged whether or not the operation is to be continued, if it is judged to be continued, the operation returns to the step 5 in FIG. 10.

In this manner, potential differences V/Vo between a plurality of predetermined positions on the DCB sensor 1 are measured, potential difference ratios V/Voi between the positions are calculated on the basis of the measured potential differences V/Vo, crack length ai is calculated from the relations between crack length and the obtained potential differences. An average crack length aj is calculated from a plurality of crack lengths ai, and crack growth rate da/dt is calculated from the average crack length aj and the crack measuring time tj. ECP is obtained from the relationships between the crack growth rate and ECP on the basis of the obtained crack growth rate da/dt, an amount of hydrogens to be injected is calculated from the obtained ECP and crack growth rate da/dt. Therefore, the dissolved oxygen concentration in nuclear reactor water, for instance, can be surely checked. Further, since hydrogen injection into the reactor water according to the calculated hydrogen injection amount and issuance of the alarm are selectively effected, the water chemistry can be monitored. Therefore, the computer 13 has a first operation part 13a for obtaining potential difference ratios through measurement by the voltmeter 10, a second operation part 13b for calculating crack length a/af and average crack length aj on the basis of the potential difference ratio, a third operation part 13c for calculating crack growth rate da/dt on the basis of the average crack length, a fourth operation part 13d for calculating ECP on the basis of the crack growth rate, and a fifth operation part 13e for calculating an amount of hydrogen to be injected from the ECP and the crack growth rate.

An embodiment of a corrosive environment control system employing the corrosive environment measuring apparatus and adopted in nuclear power plant will be described hereunder referring to FIG. 17.

In FIG. 17, the nuclear power plant includes a pressure vessel 20 of a boiling water reactor (BWR), a steam turbine 23 connected to the pressure vessel 20 by a main steam line 22, a condenser 24, a feed pump 25 mounted on a feed water line to feed water from the condenser 24 to the pressure vessel 20, recirculation lines each having a recirculation pump 26, 26', and a reactor water clean-up apparatus 28 connected to the recirculation line by a reactor clean-up line 27. The nuclear power plant is provided with the corrosive environment control system which comprises the corrosive environment measuring apparatus 5, DCB sensors 1, 1', disposed in a neutron instrument pipe 21 in the pressure vessel 20 and in a part of a recirculation pipe 34 through a T-shaped coupling, respectively, and connected to the corrosive environment measuring apparatus 5, water chemistry control system 29, a water chemistry diagnosis system 30 connected to the water chemistry control system 29, and a hydrogen injection system 31 which receives hydrogens from a hydrogen production apparatus 32 through a hydrogen storage tank 33.

In this system, the potential difference caused in the DCB sensor 1 by water in the neutron instrument pipe 21 is measured, while the potential difference caused in the DCB sensor 1' by recirculation water in the recirculation line 34 is measured. Crack length, crack growth rate and ECP each are obtained, based on the measured potential differences in the above-mentioned manner, whereby the water chemistry conditions are judged. In this case, if dissolved oxygen concentration is low, the water chemistry condition is made good by injecting hydrogens from the hydrogen injection system 31 into a line between the condenser 24 and the feed water pump 25.

At this time, in the water chemistry diagnosis system 30, an amount of hydrogen to be injected is determined on the basis of water chemistry distribution in the reactor obtained in advance through computer simulation. In this case, the water chemistry distribution may be different from a forecast distribution. Therefore, data base of relationships between hydrogen injection amount taken before and the water chemistry is prepared in the water chemistry control system 29, and the control system is provided with a function to correct a result of the computer simulation of the water chemistry diagnosis system 30. In this manner, when the water chemistry control system 29 has the correction function, even if the water chemistry distribution differs from the forecast distribution, the water chemistry diagnosis system 30 effects easily the water chemistry control and is sure to control the water chemistry to good one.

The hydrogen injection system 31 takes a prescribed amount of hydrogens from the hydrogen tank 33 to inject when the injection amount of hydrogens is determined by the water chemistry diagnosis system 30.

According to this embodiment, the water chemistry is judged from the reactor water in the neutron instrument pipe 21 and the recirculation water in the recirculation line by the two DCB sensors 1, 1', so that water chemistry control is carried out more surely and correctly. Further, in this embodiment, the water chemistry diagnosis system 30 and the water chemistry control system 31 are provided separately from the computer 13 of the corrosive environment measuring apparatus 30 in FIG. 9, and function independently therefrom. It also is possible to provide the computer 13 with such functions.

Figure 18:
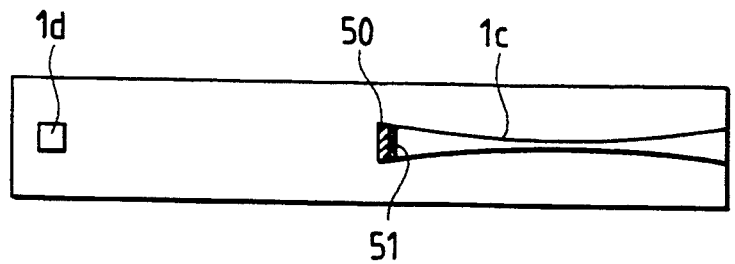
FIG. 18 is a sectional view of a DCB sensor according to further another embodiment.

A second embodiment of the DCB sensor 1 is described referring to FIG. 18. When the DCB sensor 1 as formed by machining is exposed to a corrosive environment such as reactor water, cracking due to SCC does not easily grow. This is same as when a pre-cracking 50 is formed at a tip portion of the crack growth portion by electric discharge machining.

In the present embodiment, the crack growth portion of the DCB sensor is provided with a pre-cracking 50 at the tip portion and a fatigue pre-cracking 51 contacting with the pre-cracking 50. The fatigue pre-cracking 51 is formed by inserting a wedge in the wedge insertion portion 1d of the beam portions 1a, 1b of the DCB sensor 1 which has the pre-cracking formed at the tip of the crack growth portion 1c, and loading stress at the crack growth portion 1c. The length is proper to be 0.5 mm. When forming the fatigue pre-cracking, loading too high stress intensity factor range $\Delta K$ forms a compression remaining stress region followed by formation of repetition plastic region at the cracking starting portion. Therefore, it is desirable to load the DCB sensor with a stress intensity factor range $\Delta K$ as low as possible. A proper stress intensity factor range $\Delta K$ is 10–15 MPa$\sqrt{m}$ which is right above the lower limit of crack growth.

In this manner, by providing the pre-cracking 50 and the fatigue pre-cracking 51 continuing the pre-cracking 50 at the tip of the crack growth portion 1c, a crack due to SCC can grow easily and smoothly when the DCB sensor 1 is disposed in corrosive water.

Figure 19:
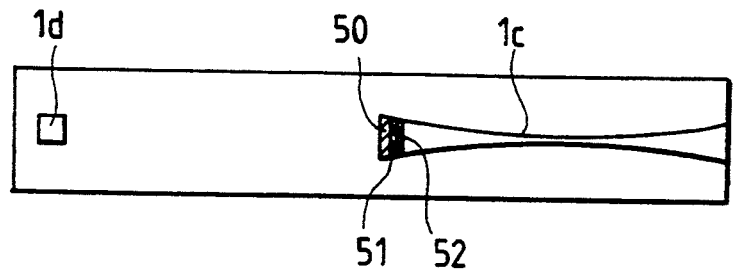
FIG. 19 is a sectional view of a DCB sensor according to further another embodiment.

A third embodiment of the DCB sensor 1 will be described referring to FIG. 19. In this embodiment, a SCC pre-cracking 52 formed by SCC is provided in addition to the pre-cracking 50 and the fatigue pre-cracking 51 as in FIG. 18. The SCC pre-cracking is a cracking really formed at the tip of the crack growth portion 1c by disposing the DCB sensor with a inserted wedge in a neutron instrument pipe of a nuclear reactor after forming the pre-cracking 50 and the fatigue pre-cracking 51. In this case, as a stress intensity factor range $\Delta K$ that load is applied, a value Kmax close to a lower limit of the crack growth, for example, Kmax of about 25 MPa$\sqrt{m}$ is better. Further, length of the SCC pre-cracking 52 is better to be about 0.2 mm.

According to this embodiment, the SCC pre-cracking 52 formed really is provided so as to continue with the fatigue pre-cracking, so that it is possible to grow surely and smoothly a crack due to SCC and the reliability of the sensor can be elevated further.

Figure 20:
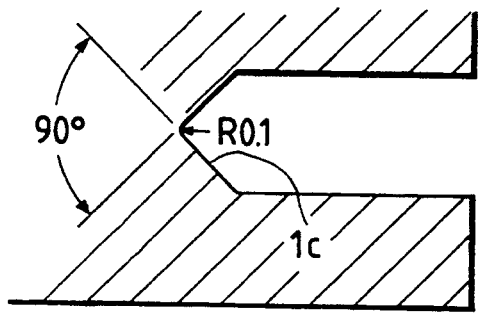
FIG. 20 is a partial sectional view of a crack growth portion according to further another embodiment.

A fourth embodiment of the DCB sensor 1 will be described, referring to FIG. 20.

In the embodiments described above, the thickness of the crack growth portion 1c is uniform all over the length from the crack starting end A to the crack terminating end B and the side faces along the length direction each are flat. According to this embodiment, however, the side faces of the crack growth portion 1c along the length direction each are V-shaped in crosssection of the crack growth portion 1c as shown in FIG. 20 in order to guide crack formed in the crack growth portion 1c to grow in the length direction of the crack growth portion. The V-shaped side faces each extend over substantially full length of the crack growth portion and have a prescribed top angle such as 90°, 60° and, at the top portion, a round shape with small radius such as 0.1 or less . If the radius is around 1 mm, the crack does not grow in the prescribed direction, and may grow toward the beam portion 1a, 1b which is smaller in ligament area. Therefore, in order for the crack to grow from a center of the thickness of the crack growth portion 1c at the tip thereof to the crack terminating end in the same plane, the radius is desirable to be 0.1 mm or less. The edge portion can be easily and precisely formed by machining.

Figure 21:
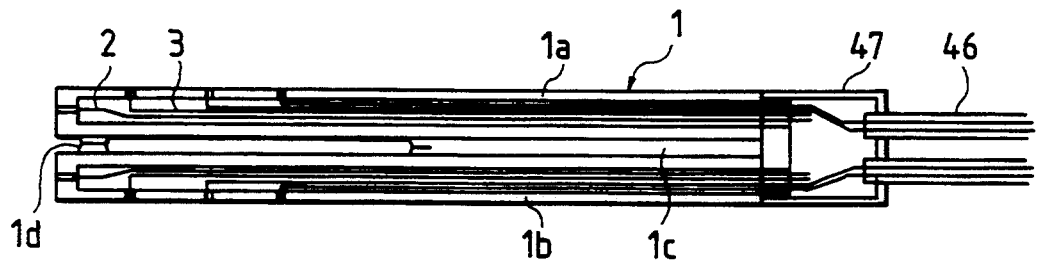
FIG. 21 is a sectional view of a DCB sensor according to further another embodiment.

A fifth embodiment of the DCB sensor 1 will be described referring to FIGS. 21 to 22.

The DCB sensor 1 is provided with two current supply leads and six measuring leads to measure crack length by a direct potential method, as previously mentioned. In the conventional connecting method for the leads, the current supply leads and the measuring leads are made of Ni, Pt, or the same material as the material of the sensor member, and the leads are connected directly to the outside of the sensor 1 by welding. When the sensor is set in a reactor, the leads may be loose parts. This embodiment is for avoiding such a trouble.

Figure 22:
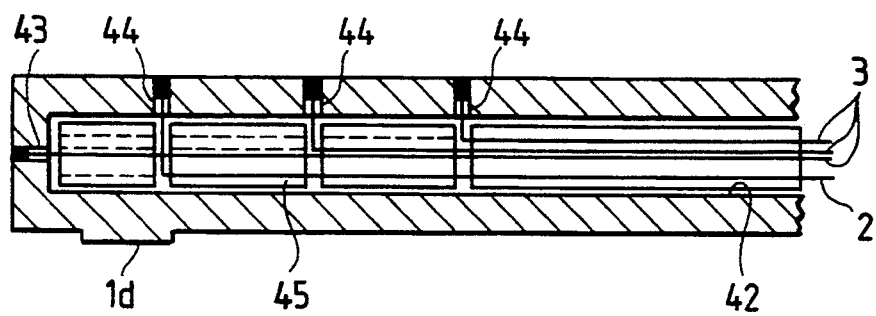
FIG. 22 is an enlarged sectional view of a part of FIG. 21.
Figure 23:
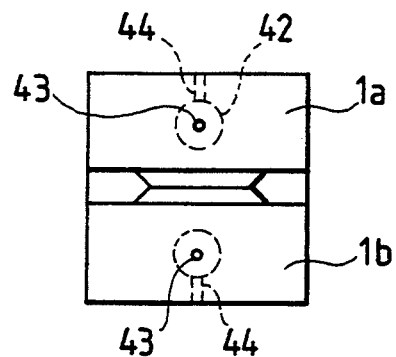
FIG. 23 is a front view of FIG. 22.

As shown in FIGS. 22 and 23, the DCB sensor 1 has first holes 42 formed in the beam portions, respectively, so as to pass through the beam portions in the length direction. Each beam portion 1a, 1b has a second hole 43 formed at the tip face thereof to communicate with the first hole 42. Each beam portion 1a, 1b has further third holes 44 at the outside to extend perpendicular to and communicate with the first hole 42. The third holes 44 are three in the number and arranged at equal intervals from the front end C of the beam portion 1a, 1b.

The current supply leads 2 each pass through the first hole 42 and one ends of the leads 2 each are inserted in the second hole 43 to be fixed firmly to the beam portion by welding. The measuring leads 3 each are inserted in the first hole 42 from the third holes 44, respectively, and the leads 3 are fixedly welded under the condition that one ends of the leads 3 are inserted in the third holes 44. In this case, in order to prevent water from penetrating into the interior of the DCB sensor 1 through the second and third holes 43, 44, the welding is effected so that the holes 43, 44 are sealed. For the welding, TIG welding or spot welding is sufficient.

Further, there are provided with a plurality of insulators 45 each of which is inserted in the first hole 42 of each of the beam portions 1a, 1b. The current supply leads 2 and the measuring leads 3 are inserted in the insulators 45. The insulators 45 are of ceramics, and the number thereof is four for each beam portion in this embodiment. In the insulator closest to the front end, only the current supply lead 2 is inserted, in the insulator 45 second closest to the front end, the current supply lead 2 and one measuring lead 3 are inserted, in the third closest insulator 45, the current supply lead 2 and two measuring leads 3 are inserted, and in the last closest insulator 45, the current supply lead 2 and all the measuring leads 3 are inserted. The last closest insulator 45 is able to be a long one which extends from the third closest insulator to the crack terminating end B. However, in order to prevent the insulator from being influenced by slight bend of the beam portion to which bending moment is applied, it is desirable to provide a series of several short insulators connected flexibly to each other, each being, for example, 10 mm long.

Figure 24:
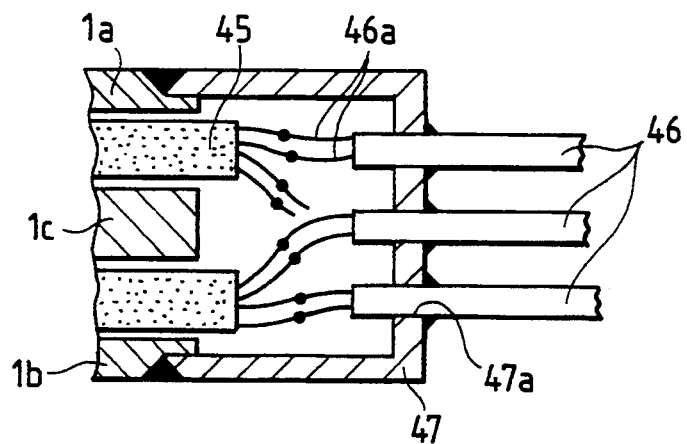
FIG. 24 is an enlarged sectional view of another part of FIG. 21.
Figure 25:
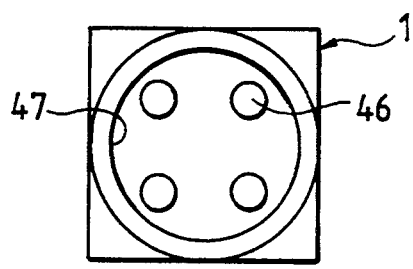
FIG. 25 is a backside view of FIG. 24.

On the other hand, the two current supply leads 2 and the six measuring leads 3 inserted in the first holes 42 of the beam portions 1a, 1b are connected to four insulation cables each having two-core leads by welding. As shown in FIG. 24, each of the insulation cables is a sheath type MI cable 46. The leads of the MI cables 46 are connected to ends of the leads 2, 3 by spot welding. In this case, if reactor water penetrates into the MI cables 46, the reactor water may leak out of the MI cables 46 through covering portions made of MgO, $Al_2O_3$, etc. In order to prevent this phenomenon, a cap 47 is fixed to the crack terminating end B by welding and prevents the reactor water from entering the interior of the beam portions 1a, 1b. As shown in FIGS. 24, 25, the cap 47 is formed so that a circular column portion formed at the crack termination end of the DCB sensor 1 is inserted in an opening portion of the cap 47. The cap 47 has through holes 47a for the MI cables 46. The cables are inserted in the through holes 47a and the peripheral portions around the cables 46 are welded to keep air tight condition between the inside and the outside of the cap 47.

According to this embodiment, various parts of the DCB sensor 1 including various leads 2, 3, the cap 47 are fixed by insertion and welding. Therefore, the parts do not become loose. Further, water penetration can be surely avoided.

A sixth embodiment of the DCB sensor will be described referring to FIGS. 26 to 29.

FIGS. 26 to 29 show a construction of preventing the parts from becoming loose.

Figure 26:
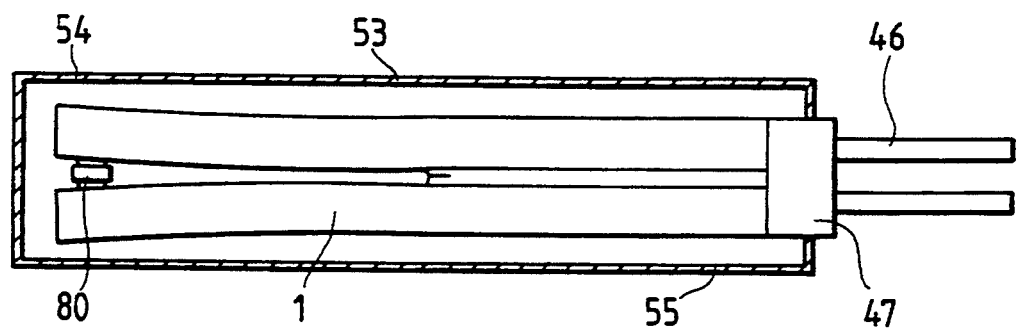
FIG. 26 is a sectional view of a DCB sensor according to further another embodiment.

In FIG. 26, if a crack in the DCB sensor 1 grows and the load applied on the wedge 80 inserted between the beam portions for a fixed displacement is reduced, the wedge 80 may be removed from the wedge inserting portion 1d, and may be a loose part. In this embodiment, a sleeve 53 for enclosing the DCB sensor 1 is provided and the DCB sensor 1 is enclosed in the sleeve 53. The sleeve 53 is fixed sealingly to the cap 47.

Describing more in detail, the sleeve 53 is formed in a cylindrical shape and has an opening at one end through which the DCB sensor 1 with the wedge 80 is inserted and at which the cap 47 is fixed by welding. The sleeve 53 has an inlet opening 54 for reactor water at an upper side around the front end and an outlet opening 55 for reactor water at a lower side around the rear end. The DCB sensor 1 with the sleeve 53 is disposed at a prescribed place in the reactor. The reactor water enters the sleeve 53 at the inlet opening 54 and goes out therefrom at the outlet opening 55 after flowing within the sleeve 53. If the wedge 80 is removed from the wedge inserting portion 1d, the wedge 80 is retained within the sleeve 53 without flowing out from any of the inlet opening 54 and the outlet opening 55. The DCB sensor 1 is the same as in FIGS. 21 to 25.

Using the sleeve 53, even if the wedge 80 is separated from the DCB sensor 1, the wedge 80 does not flow out of the sleeve 53. Therefore, the wedge 80 is prevented from becoming a loose part.

Figure 27:
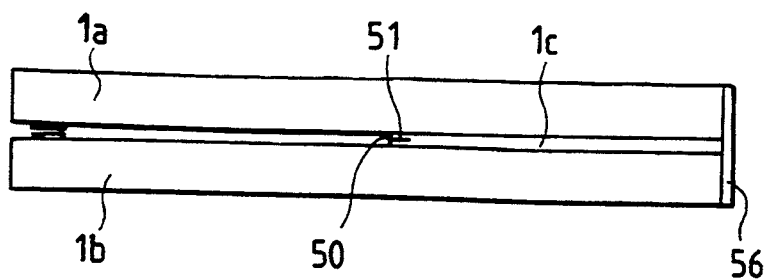
FIG. 27 is a side view of a DCB sensor according to further another embodiment.

Another embodiment of the DCB sensor 1 is shown in FIG. 27.

In this embodiment, a thin plate 56 made of the same material as material of the DCB sensor member is mounted on the rear end of the sensor. In this construction, even if a crack grows from the starting end to the termination end, the beam portions 1a, 1b of the DCB sensor 1 are not separated from each other and connected by the thin plate 56. Therefore, the sensor itself does not become loose parts. In this case, the thin plate 56 is preferable to be extremely thin not to change the strength of the beam portions 1a, 1b. In this embodiment, it is about 0.5 mm thick.

Figure 28:
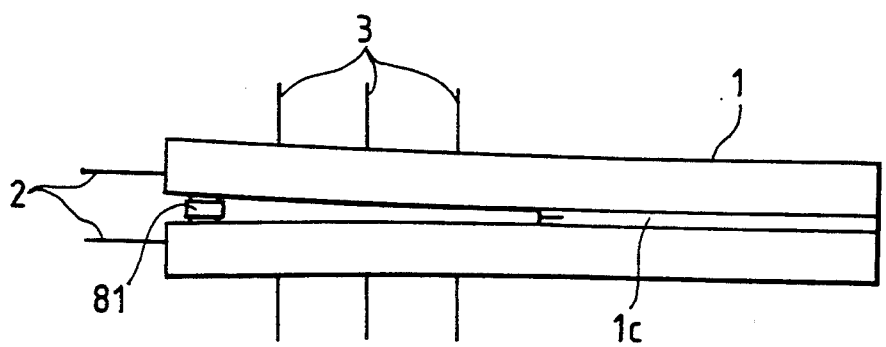
FIG. 28 is a side view of a DCB sensor according to further another embodiment.

Another embodiment of the DCB sensor 1 is shown in FIG. 28.

In this embodiment, a wedge 81 inserted between the beam portions 1a, 1b is fixed to the beam portion by welding, whereby the wedge 81 is prevented from becoming a loose part. In this case, when direct current is applied on the beam portions 1a, 1b for measuring crack length, current flowing into the crack growth portion 1d may decrease drastically in accordance with kinds of material used for the wedge 81. Therefore, the wedge 81 is made of the same material as the DCB sensor member, whereby the decrease of current flow to the crack growth portion 1d is suppressed.

Figure 29:
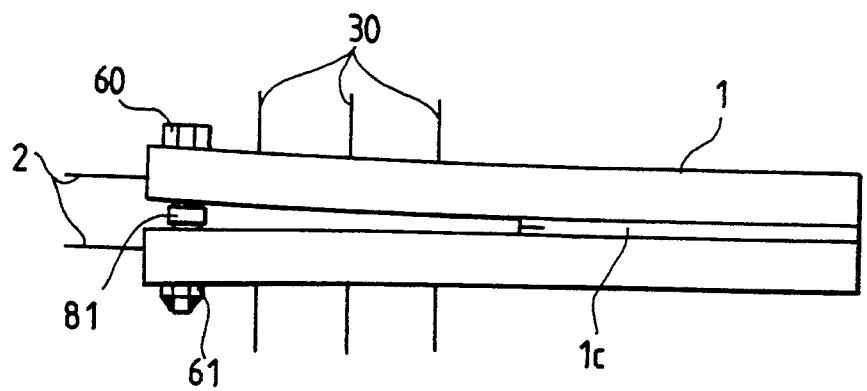
FIG. 29 is a side view of a DCB sensor according to further another embodiment.

Another embodiment of the DCB sensor is shown in FIG. 29.

In FIG. 29, the beam portions 1a, 1b and the wedge 81 each have a through hole for a bolt. After the wedge 81 is inserted in the wedge inserting portion 1d of the DCB sensor 1, a bolt 60 is inserted in the through holes and screwed by a nut 61 to fasten. Then, the bolt 60 and the nut 61 are welded. In this construction, even if the crack grows all over the length of the crack growth portion 1c, the beam portions 1a, 1b are separated from each other and prevented from becoming loose parts because they are connected at the wedge 81.

Figure 30:
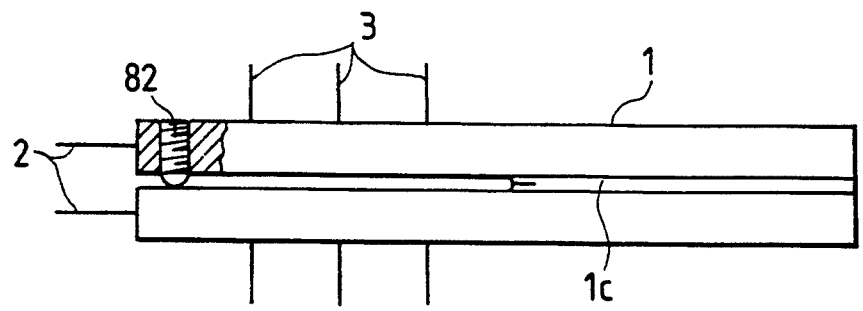
FIG. 30 is a partial sectional view of a DCB sensor according to further another embodiment.
Figure 31:
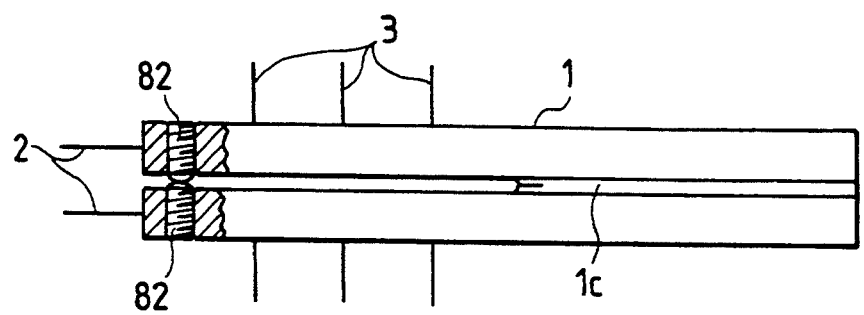
FIG. 31 is a partial sectional view of a DCB sensor according to further another embodiment.
Figure 32:
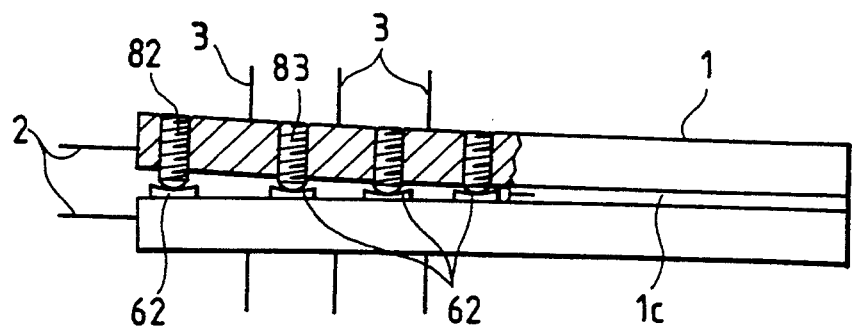
FIG. 32 is a partial sectional view of a DCB sensor according to further another embodiment.

Another embodiment of the DCB sensor is shown in FIGS. 30 to 32.

In FIG. 30, a screw hole is formed in one 1a of the beam portions 1a, 1b at the front end portion. A wedge 82, made of conductive material and having a screw formed on periphery thereof is screwed into the screw hole to press the other beam portion 1b, whereby a fixed displacement is caused in the beam portions 1a, 1b. The wedge 82 has a semi-spherical shape at a tip which contacts with the beam portion 1b, whereby the contacting tip of the wedge 81 can easily move relatively to the beam portion 1b when the wedge 82 is screwed and can be free from applying unnecessary bending load to the beam portion.

FIG. 31 shows a modification of FIG. 30. In FIG. 30, a pair of wedges 82 are prepared, each of which has a semi-spherical tip and a screwed outer surface. The wedges 82 are screwed into screw holes formed in the beam portions 1a, 1b so that the tips of the wedges 82 press each other to cause a fixed displacement in the beam portions 1a, 1b. In this case, the tips are formed into semi-spherical shape so that the wedge tips can move, thereby not to load unnecessary bending load on the beam portions 1a, 1b.

Another embodiment of the DCB sensor is described referring to FIG. 32.

In FIG. 32, the wedge 82 which is the same as in FIG. 31, and three wedges 83 are prepared. Each wedge has a screwed outer surface and a semi-spherical tip. The wedges 82, 83 are screwed into screw holes formed in one 1a of the beam portions 1a, 1b, at a proper intervals and received by concave porions 61 formed in the other beam portion 1b at the tips of the wedges. The wedge 82 which is closest to the front end of the sensor 1 causes a fixed displacement in the beam portions 1a, 1b. The other wedges 83 are for adjusting fastening torque to be uniform thereby applying a fixed displacement on the beam portions 1a, 1b. Upon adjusting the fastening torque for the wedges 83, the adjustment is effected precisely using an instrument or device for measuring fastening torque magnitude. In this embodiment, the sensor has one wedge 82 for applying a prescribed displacement at the tip of the beam portions 1a, 1b, and a plurality of wedges 83 for applying and keeping the initial displacement.

Another embodiment of the DCB sensor will be described referring to FIGS. 33 to 34.

In the above mentioned embodiments, the form of the crack growth portion 1c is changed so that the stress intensity factor ΔK can be kept constant. In this embodiment, the shape of the crack growth portion 1c is the same as conventional one, that is, the width of the crack growth portion 1c is constant, and a load loaded on the beam portions 1a, 1b is changed according to change in the length of a crack caused in the crack growth portion 1c so that the stress intensity factor ΔK at the tip of the crack can be kept constant.

Figure 33:
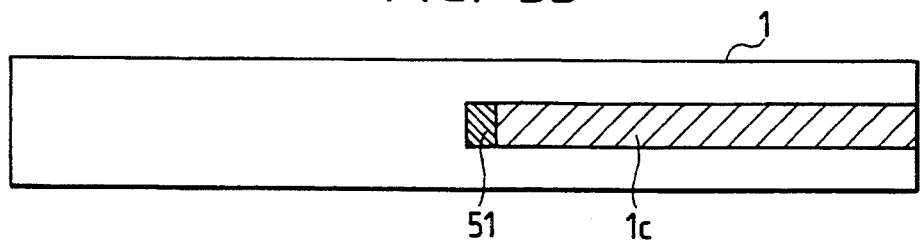
FIG. 33 is a sectional view of a DCB sensor according to further another embodiment.
Figure 34:
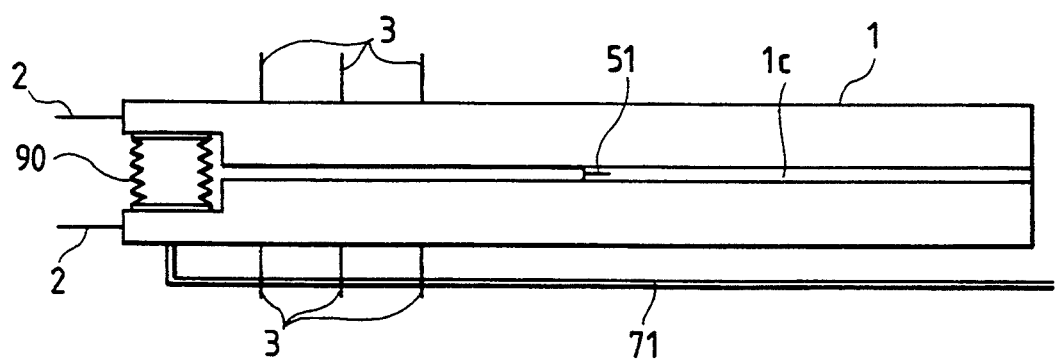
FIG. 34 is side view of the DCB sensor in FIG. 33.

Namely, the DCB sensor 1 according to the embodiment has a straight and constant width of the crack growth portion 1c as shown in FIG. 33 and a fatigue pre-crack 51 formed at the crack starting point. As shown in FIG. 34, a wedge inserting portion is formed, at front end portion of the sensor, between the opposite beam portions 1a, 1b. An expansible wedge 90 is inserted in the wedge inserting portion. The wedge 90 is a small sized expansible chamber for example, a small sized piston and cylinder unit. The expansible chamber or cylinder 90 is connected to a pressurized fluid feed pipe 71 through a passage 70 formed in one 1b of the beam portions. A working fluid such as compressed air, pressurized liquid is introduced into the wedge 90. As a crack grows, load applied on the beam portions 1a, 1b is changed by the wedge 90. As the crack grows, the wedge 90 expands according to the length of the crack, whereby the stress intensity factor ΔK at the tip of the crack can be always kept constant. Further, the wedge 90 can be fixed to the beam portions 1a, 1b by a fixing means, or an insulator can be inserted between the wedge 90 and one of the beam portions.

By the way, in the DCB sensor, the crack growth portion width of which is constant as mentioned above, the stress intensity factor ΔK decreases as crack grows as shown in FIG. 11. In general, deflection δ of a beam is given as follows;

$$\delta = -Wl^3/3EI.$$

When the displacement is constant, a load W decreases proportionally to the third powers of crack length l, so that the following relation with respect to an initial load Wo is given;

$W/Wo = (lo/l)$, in which E is Young's modulus and I is geometrical moment of inertia. Accordingly, when a load at an initial crack length a=45 mm is taken as a standard, there are the following relations as in table:

|  |  | Crack length | | | | | | |
| --- | --- | --- | --- | --- | --- | --- | --- | --- |
| a |  | 45 | 50 | 55 | 60 | 65 | 70 | 75 |
| Load ratio | W/Wo | 1.0 | 0.729 | 0.548 | 0.422 | 0.332 | 0.266 | 0.216 |
| K value ratio | K/Ko | 1.0 | 0.891 | 0.781 | 0.672 | 0.564 | 0.453 | 0.344 |
| Set load ratio | W/Wo' | 1.0 | 0.819 | 0.701 | 0.629 | 0.589 | 0.586 | 0.629 |

On the other hand, a stress intensity factor ΔK decreases proportionally to an increment of crack length, as shown in FIG. 5. In order to make the value of ΔK constant, the load is necessary to satisfy the following relation;

$$W/Wo' = 1/(K/Ko).(W/Wo).$$

Figure 35:
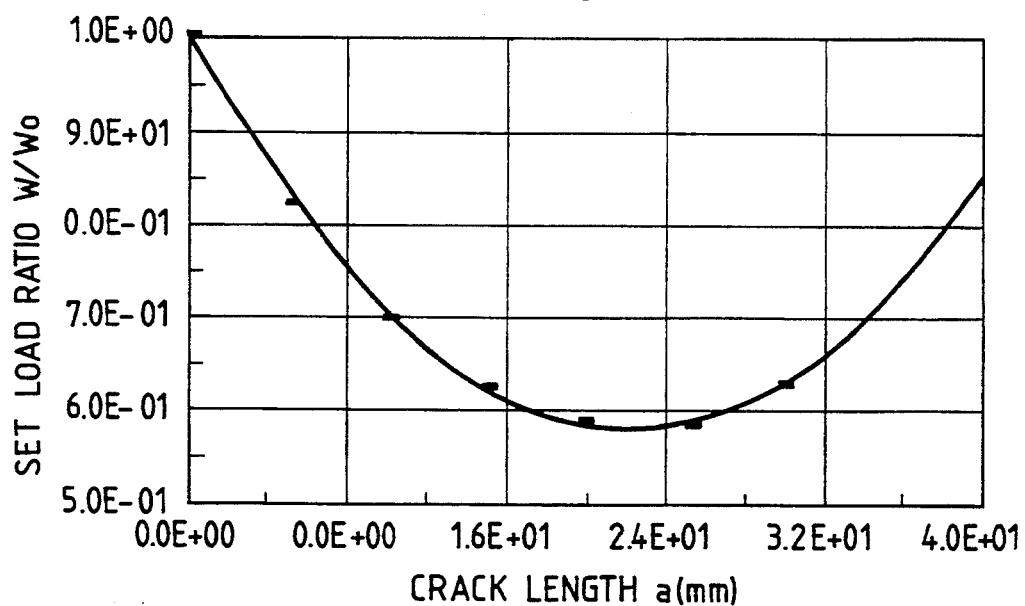
FIG. 35 is a diagram showing the relationship between set road ratios and crack length.

This is as shown in the above table and FIG. 35. The relations between the load and the crack length is given as follows:

$$W/Wo' = 1.0 - 0.0377a + 0.00085a.$$

The pressure adjustment of the wedge 90 is sufficient to be done at each crack growth length Δa=0.2 mm.

Further, when the wedge 90 is a piston and cylinder unit, it is preferable to use an O-ring made of stainless steel between the piston and cylinder to maintain the pressure in the cylinder.

A construction and an operation of the DCB sensor 1 with the above-mentioned wedge 90 will be described referring to FIG. 36. A measuring method of crack length of the DCB sensor is the same as the above-mentioned method. Therefore, only a wedge control is explained hereunder.

Figure 36:
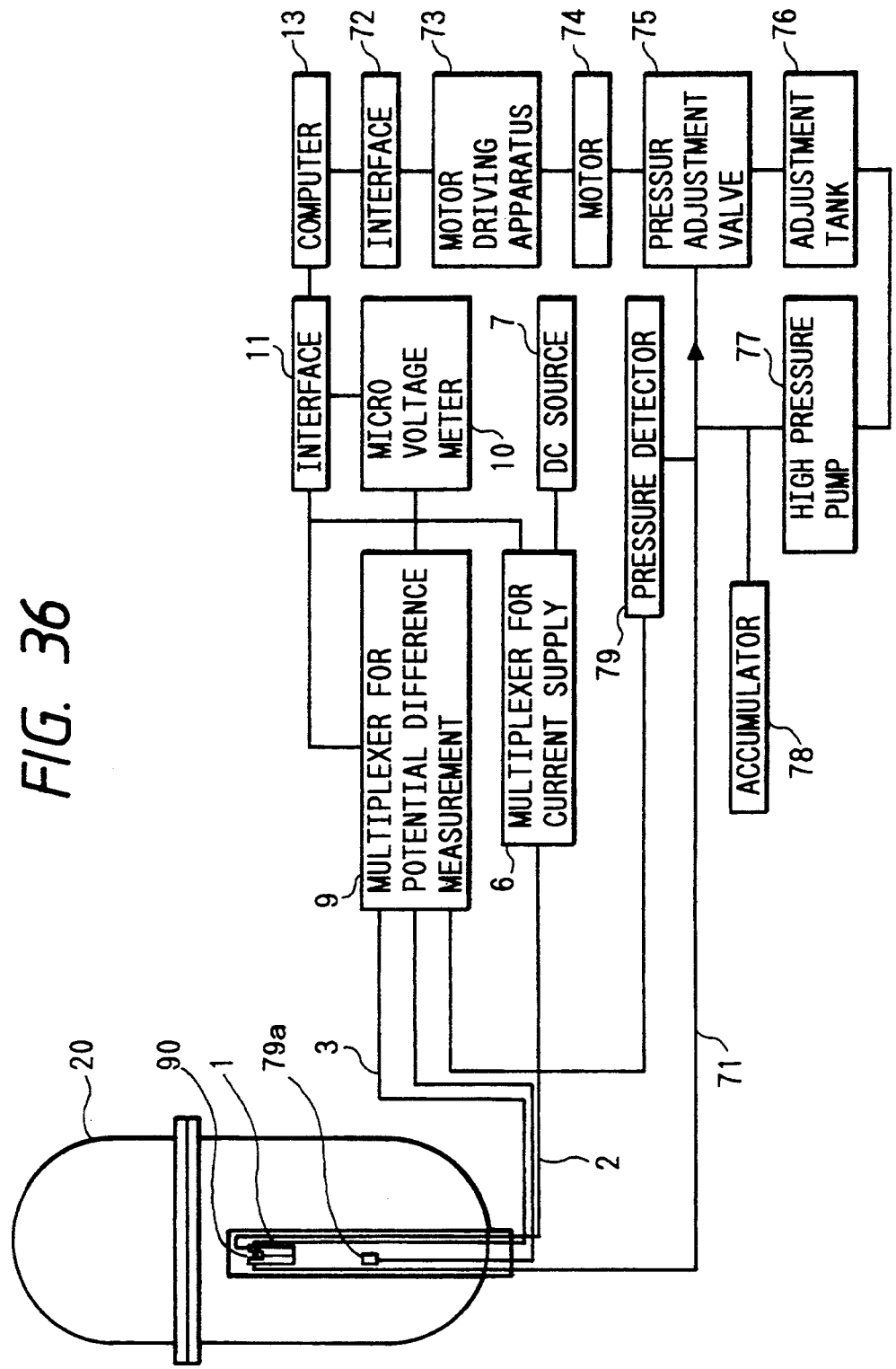
FIG. 36 is block diagram of a control apparatus of the DCB sensor in FIGS. 33, 34 by a corrosive environment measuring apparatus.

In FIG. 36, the DCB sensor 1 comprises the above-mentioned wedge 90, and a control means for controlling the wedge according to crack length. The control means comprises crack length measuring means for measuring crack length such as the corrosive environment measuring apparatus as shown in FIG. 9.

The control means comprises an adjustment tank 76 for containing a fluid such as pure water, a pressure adjusting valve 75 for adjusting the pressure of the fluid, a motor 74 connected to the valve 75 for driving the valve 75, a motor driving apparatus 73, electrically connected to the crack length measuring means, for driving the motor according to signals from the crack length measuring means, an accumulator 78 and a high pressure pump 77 fluidly connected to the adjustment tank 76, the accumulator 78, the wedge 90 and the pressure adjusting valve 75. The pump 77 sucks the fluid from the adjustment tank 76 and delivers the fluid to the accumulator 78 and return it into the adjustment tank 76 through the valve 75. The valve 75 is controlled of an opening thereof to adjust the pressure of the fluid. The adjusted pressure fluid is applied to the wedge 90 through the fluid feed pipe 71 to control the expansion of the wedge 90.

Since the pressure of reactor water in a reactor vessel 20 is high, it is necessary to add the pressure of the reactor water to the wedge 90 in addition to the pressure for applying a load to the DCB sensor 1 by the wedge 90 when the DCB sensor 1 is disposed in the reactor water. Therefore, the fluid feed pipe 71 has the pressure detector 79 mounted thereon for detecting the pressure of the fluid in the pipe 71. Further, a pressure detector 80 is provided in the pressure vessel 20 to detect the pressure of the reactor water. When a crack in the DCB sensor 1 grows, the computer 13 of the crack measuring means outputs to the motor driving apparatus 73 such a signal for adjusting the valve 75 through the motor 74 that the pressure of the fluid in the fluid feed pipe 71 will be the water pressure in the reactor vessel 20 detected by the detector 80 plus the pressure necessary for loading the DCB sensor 1 by the wedge 90 in the atmosphere according to the length of the crack in the DCB sensor 1, and the expansion of the wedge 90 is controlled, whereby the stress intensity factor at the cracking tip is kept constant. The pressure control of the wedge 90 is effected at each crack growth of 0.2 mm.

In this manner, the wedge 90 is expanded according to the crack length in the crack growth portion of the DCB sensor 1, so that the stress intensity factor can be kept nearly constant even if the width of the crack growth portion 1c is uniform in the length direction. The DCB sensor 1 can be used surely as a corrosive environment sensor.

The wedge 90 can be replaced by a bellows. In this case, the construction can be more simplified.

The DCB sensor according to the present invention has the effect that stress intensity factor at a portion that a crack is occurring can be kept nearly constant. By producing the DCB sensor so that the crack growth portion has a maximum width of at most 0.2 times width of the beam portion, a minimum width of at least 1 mm and a total height of the beam portions are equal to or larger than the width of the beam portions, bending moment caused in the beam portions is reduced, and by providing the DCB sensor with the V-shaped recess at each side of the crack growth portion, a crack can grow in the same plane and measuring of the crack length can be effected well, whereby the reliability thereof can be raised even if the sensor is used in a high temperature environment such as in high temperature water in a BWR. By producing the crack growth portion so as to be free from a high remaining tensile stress, it is prevented that a crack growth rate becomes remarkably large. Further, by producing at least the surface of the wedge with an insulating material, current does not flow in the wedge when direct current is applied, so that it is prevented that preciseness of crack length measurement is reduced. It is apparent from the description of the embodiments that the present inventions have various advantages or effects in addition to the right above-mentioned.

What is claimed is:

1. A double cantilever type sensor comprising:
   an elongate metal member having a crack growth portion, formed therein, extending in a length direction of said member from a crack starting end to crack terminating end, and having a pair of opposite sides defining a width of said crack growth portion, said pair of opposite sides each extending in the length direction of said member to form a first circular arc with a first radius from said crack starting end to an intermediate location of said crack growth portion and a second circular arc with a second radius less than said first radius from said intermediate location toward said crack terminating end, the width of said crack growth portion decreasing from said crack starting end to said intermediate location and increasing from said intermediate location toward said crack terminating end such that a crack growth portion has a substantially constant stress intensity factor at the crack growth portion; and
   a wedge for applying a load to said crack growth portion.

2. A corrosive environment control system comprising:
   a corrosive environment sensor disposed in a reactor water and comprising an elongate member having a crack growth portion, formed therein, extending in a length direction of said member from a crack starting end to a crack terminating end, and having a pair of opposite sides defining a width of said crack growth portion, said pair of opposite sides each extending in the length direction of said member to form a first circular arc with a first radius from said crack staring end to an intermediate position of said crack growth portion and a second circular arc with a second radius less than said first radius from said intermediate position toward said crack terminating end, the width of said crack growth portion decreasing from said crack starting end to said intermediate position and increasing from said intermediate position toward said crack terminating end such that a crack growth portion has a substantially constant stress intensity factor at the crack growth portion, and a wedge for applying a load to said crack growth portion;
   a current supply system for supplying direct current to said corrosive environment sensor and switching the polarity of the direct current;
   potential measuring means for measuring potential differences between a plurality of predetermined positions of said corrosive environment sensor;
   means for judging water chemistry of said reactor water by a direct current method, said measuring means including a function of attaining potential difference ratios on the basis of the measured potential differences, a function of attaining a crack growth rate and electrochemical potential (ECP) from a relationship between said measured potential differences and crack length, and a relationship between crack growth rates and ECP, on basis of potential differences, and a function of judging the water chemistry;
   means for calculating a hydrogen injection amount on basis of the obtained ECP and crack growth rate; and
   means for injecting hydrogen into the reactor water according to the water chemistry.

3. A corrosive environment measuring apparatus comprising:
   a corrosive environment sensor disposed in a reactor water and comprising an elongate member having a crack growth portion, formed therein, extending in a length direction of said member from a crack starting end to a crack terminating end, and having a pair of opposite sides defining a width of said crack growth portion, said pair of opposite sides each extending in the length direction of said member to form a first circular arc with a first radius from said crack starting end to an intermediate position of said crack growth portion and a second circular arc with a second radius less than said first radius from said intermediate position toward said crack terminating end, the width of said crack growth portion decreasing from said crack starting end to said intermediate position and increasing from said intermediate position toward said crack terminating end such that a crack growth portion has a substantially constant stress intensity factor at the crack growth portion, and a wedge for applying a load to said crack growth portion;
   a current supply system for supplying direct current to said corrosive environment sensor and switching the polarity of the direct current;
   potential measuring means for measuring potential differences between a plurality of predetermined positions of said corrosive environment sensor; and
   control means for judging water chemistry of said reactor water by a direct current method, said control means including a function of attaining potential difference ratios on the basis of the measured potential differences, a function of attaining a crack growth rate and electrochemical potential (ECP) from a relationship between said measured potential differences and crack length, and a relationship between crack growth rates and ECP, on basis of potential differences, and a function of judging the water chemistry.

4. A corrosive environment measuring apparatus according to claim 3 wherein said first radius and said second radius each have a center thereof on a line distant from said crack terminating end toward said crack starting end by a predetermined distance, the width of said crack growth portion decreasing from said crack starting end to said line and increasing from said line to said crack terminating end, and wherein said predetermined distance is 15–20 mm to a length of 100 mm of said beam portion, and said first and second radii are 110–160 mm and 60–75 mm, respectively.

5. A corrosive environment measuring apparatus comprising:
a corrosive environment sensor disposed in a corrosive environment and comprising an elongate member having a crack growth portion, formed therein, extending in a length direction of said member from a crack starting end to a crack terminating end, and having a pair of opposite sides defining width of said crack growth portion, said pair of opposite sides each extending in the length direction of said member to form a first circular arc with a first radius from said crack starting end to an intermediate position of said crack growth portion in the length direction, and a second circular arc with a second radius less than said first radius from said intermediate position toward said crack terminating end, the width of said crack growth portion decreasing from said crack starting end to said intermediate position and increasing from said intermediate position toward said crack terminating end such that a crack growth portion has a substantially constant stress intensity factor at the crack growth portion, and a wedge for applying a load to said crack growth portion;
a current supply system for supplying direct current to said corrosive environment sensor and switching the polarity of the direct current;
potential measuring means for measuring potential differences between a plurality of predetermined positions of said corrosive environment sensor; and
control means for measuring the degree of said corrosive environment in which said corrosive environment sensor is disposed, by a direct current method, said control means including a function of attaining potential difference ratios on the basis of the measured potential differences, a function of attaining a crack growth rate and electro-chemical potential (ECP) from a relationship between said measured potential differences and crack length, and a relationship between crack growth rates and ECP, on basis of potential differences, and a function of measuring the degree of said corrosive environment.

6. A corrosive environment measuring apparatus according to claim 5, wherein said first radius and said second radius each have a center thereof on a line distant from said crack terminating end toward said crack starting end by a predetermined distance, the width of said crack growth portion decreasing from said crack starting end to said line and increasing from said line to said crack terminating end, and wherein said predetermined distance is 15–20 mm to a length of 100 mm of said beam portion, and said first and second radii are 110–160 mm and 60–75 mm, respectively.

7. A corrosive environment measuring apparatus according to claim 5, wherein said control means includes means for obtaining potential difference ratio on the basis of measured potential differences, means for calculating crack length from a relationship between the potential difference ratios and crack length based on the potential difference ratios, and calculating an average crack length between the plurality of positions, means for obtaining a crack growth rate on the basis of the average crack length, means for obtaining ECP from the relationship between the crack growth rate and the ECP on the basis of the crack growth rate, and means for calculating a hydrogen injection amount on basis of the obtained ECP and crack growth rate.

8. A corrosive environment sensor comprising:
a sensor member of one piece having a pair of beam portions formed so as to oppose each other, the sensor member having first and second ends, the pair of beam portions extending between the first and second ends, the pair of beam portions having first surfaces spaced from and facing each other, the sensor member having a crack growth portion formed between said pair of beam portions so as to extend in a length direction of said sensor member, said length direction being a direction between the first and second ends of the sensor member, said crack growth portion extending from an intermediate position of the sensor member, between the first and second ends and spaced from the first end, toward the second end of the sensor member; and
a wedge inserted between said pair of beam portions at around said first end,
wherein said crack growth portion has a width defined by a pair of sides extending between the pair of beam portions, said pair of sides each including (a) first side portions extending from the intermediate position of the sensor member toward the second end, to an intermediate location of the crack growth portion, the first side portions extending such that a part of the crack growth region defined by the first side portions decreases in width from the intermediate position of the sensor member to the intermediate location of the crack growth region, and (b) second side portions extending from the intermediate location of the crack growth region toward the second end of the sensor member, the second side portions extending such that a part of the crack growth region defined by the second side portions increases in width from the intermediate location of the crack growth region toward the second end of the sensor member, each of the first side portions and the second side portions being defined by quadratic curves such that a crack growth portion has a substantially constant stress intensity factor at the crack growth portion.

9. A corrosive environment sensor according to claim 8, wherein a thickness of the crack growth portion, in a direction extending between the first surfaces of the pair of beam portions, is uniform along the length direction of the sensor member.

10. A corrosive environment sensor according to claim 8, wherein a width of the crack growth portion at an end thereof closest to the second end of the sensor member is less than widths of the pair of beam portions at the second end.

11. A corrosive environment sensor according to claim 8, wherein the quadratic curves defining the first and second side portions are such that a stress intensity factor of the sensor, at a crack growing point, remains substantially constant during crack growth in the crack growth portion.

12. A corrosive environment sensor according to claim 8, wherein said quadratic curves of the first side portions consists of a first circular arc with first radius, between said intermediate position of said sensor member and said intermediate location of said crack growth portion, and said quadratic curves of each of the second side portions consists of a second circular arc with second radius less than said first radius, between said intermediate location of said crack growth portion and around said second end of said sensor member.

13. A corrosive environment sensor according to claim 12, wherein said crack growth portion is formed by machining so as to be free from remaining tensile stress.

14. A corrosive environment sensor according to claim 12, wherein a thin plate of a same material as a material of said sensor member is fixed to both of said beam portions at said second end of said sensor member by welding.

15. A corrosive environment sensor according to claim 12, wherein said wedge is made of a same material as a material of said sensor member, and is fixed to said beam portions around said first end by spot welding.

16. A corrosive environment sensor according to claim 12, wherein there is provided fixing means passing through and fixing said beam portions and said wedge.

17. A corrosive environment sensor according to claim 12, wherein said wedge has a screw formed on a periphery thereof and a round tip, said wedge is screwed into a screw portion formed in one of said beam portions so that said round tip presses the other beam portion.

18. A corrosive environment sensor according to claim 12, wherein said wedge consists of two wedge pieces each having a screw formed on a periphery thereof and a round tip, said wedge pieces each being screwed into a screw portion formed in each of said beam portions so that said tips contact and press each other.

19. A corrosive environment sensor according to claim 12, wherein said wedge has a screw formed on a periphery thereof and a round tip, said wedge is screwed into a screw portion formed in one of said beam portions at a position close to said first end of said sensor member so that said round tip presses the other beam portion to cause a fixed displacement in said beam portions, and at least two further wedges are included, said further wedges each having a screw formed on a periphery thereof and a round tip, and said further wedges being screwed into screw portions formed in said one of said beam portions between said wedge and a crack starting end of said crack growth portion at prescribed intervals to impart displacement to said beam portions.

20. A corrosive environment sensor according to claim 12, wherein at least one surface of said wedge is of an insulating material.

21. A corrosive environment sensor according to claim 12, wherein said sensor member is cut off from a rolled plate so that the length direction of said beam portions is in a rolling direction of said plate, a displacement direction of said beam portions is perpendicular to said rolling direction in a plane in parallel to a rolling surface of said plate.

22. A corrosive environment sensor according to claim 12, wherein said crack growth portion has a pre-crack portion formed by electric discharge at a crack starting end and a fatigue pre-crack portion formed by effecting fatigue at a tip of said pre-crack portion so as to continue in the length direction.

23. A corrosive environment sensor according to claim 22, wherein a stress corrosion cracking pre-crack portion is provided at a tip portion of said fatigue pre-crack portion by actually causing stress corrosion cracking at said tip of said fatigue pre-crack portion.

24. A corrosive environment sensor according to claim 12, wherein said beam portions each have a first through hole passing therethrough from said second end to said first end and a plurality of second holes formed therein at regular intervals so as to extend in a direction traversing said first through hole from said first through hole to the outside of said beam portion, wherein said sensor further includes current supply leads each being inserted in said first through hole through a plurality of insulators inserted in said first through hole, with one end thereof being fixed to said beam portion at said first end and the other end being disposed around said second end, a plurality of measuring leads being inserted in said first through hole through said insulators with one ends thereof being inserted in said second holes, respectively, and fixed to said beam portion and the other end being disposed around said second ends, a cap being disposed so as to enclose said beam portions at said second end of said sensor member and air-tightly fitted to said beam portions, and insulating cables passing through and airtightly fixed to said cap, with one ends thereof being connected to said leads in said cap.

25. A corrosive environment sensor according to claim 24, further including an enclosure having an opening at one end thereof and enclosing therein said beam portions, said wedge and all said leads through said opening air tightly fitted to said cap, said enclosure having a fluid inlet and a fluid outlet, the size of each of said inlet and said outlet being such that said wedge can not pass therethrough.

26. A corrosive environment sensor according to claim 12, wherein said sensor member is made of a material high in sensibility of stress corrosion cracking and high in yield stress.

27. A corrosive environment sensor according to claim 26, wherein said material is a stainless steel having a designation of SUS 304, and carbon of 0.05 wt % or more.

28. A corrosive environment sensor according to claim 12, wherein said crack growth portion has a maximum width of at most 0.2 times a width of said beam portions and a minimum width of at least 1 mm, and a height of the beam portions equal to or larger than the width of said beam portions.

29. A corrosive environment sensor according to claim 28, wherein sides of said crack growth portion defining the width each are formed in a V-shaped recess extending in the length direction of said sensor member, the V-shaped recess having a tip at a deepest penetration of the recess into the crack growth portion, the tip being rounded with a radius of at most 0.1 mm.

30. A corrosive environment sensor according to claim 29, wherein a thickness of the crack growth portion, in a direction extending between the first surfaces of the pair of beam portions, is uniform along the length direction of the sensor member.

31. A corrosive environment sensor according to claim 12, wherein said crack growth portion has a crack starting end and a crack terminating end, and said first radius and said second radius each have a center thereof on a line distant from said crack terminating end toward said crack starting end by a predetermined distance, the width of said crack growth portion decreasing from said crack starting end to said line and increasing from said line to said crack terminating end, and wherein said predetermined distance is 15-20 mm to a length of 100 mm of said beam portion, and said first and second radii are 110-160 mm and 60-75 mm, respectively.

32. A corrosive environment sensor according to claim 31, wherein said crack growth portion has a maximum width of at most 0.2 times a width of said beam portions, a minimum width of at least 1 mm, and a height, which is a distance between the first surfaces of said beam portions, equal to or larger than the minimum width.

33. A corrosive environment sensor according to claim 32, wherein each of the sides of said crack growth portion defining the width is formed in a V-shaped recess extending in the length direction of said sensor member, the V-shaped recess having a tip at a deepest penetration of the recess into the crack growth portion, the tip being rounded with a radius of at most 0.1 mm.

34. A corrosive environment sensor according to claim 33, wherein a thickness of the crack growth portion, in a direction extending between the first surfaces of the pair of beam portions, is uniform along the length direction of the sensor member

* * * * *